United States Patent [19]

Coy et al.

[11] Patent Number: 5,416,073
[45] Date of Patent: May 16, 1995

[54] GROWTH HORMONE-RELEASING PEPTIDES AND METHOD OF TREATING ANIMALS, THEREWITH

[75] Inventors: David H. Coy, New Orleans; William A. Murphy, Slidell, both of La.

[73] Assignee: The Adminstrators of the Tulane Educational Fund, New Orleans, La.

[21] Appl. No.: 807,821

[22] Filed: Dec. 16, 1985

Related U.S. Application Data

[63] Continuation-in-part of Ser. No. 692,082, Jan. 7, 1985, which is a continuation-in-part of Ser. No. 605,520, Apr. 30, 1984, abandoned, which is a continuation-in-part of Ser. No. 522,067, Aug. 10, 1983, abandoned.

[51] Int. Cl.⁶ .................. A61K 37/36; C07K 7/00
[52] U.S. Cl. ............................ 514/12; 530/324; 530/350; 530/399
[58] Field of Search .............. 514/12; 530/399, 350, 530/324

[56] References Cited

U.S. PATENT DOCUMENTS

| | | | |
|---|---|---|---|
| 4,127,518 | 11/1978 | Coy et al. | 260/8 |
| 4,127,540 | 11/1978 | Coy et al. | 260/8 |
| 4,127,541 | 11/1978 | Coy et al. | 260/8 |
| 4,180,501 | 12/1979 | Coy et al. | 260/112.5 R |
| 4,213,968 | 8/1980 | Kastin et al. | 424/177 |
| 4,317,770 | 3/1982 | Li | 260/112.5 E |
| 4,529,595 | 7/1985 | Rivier et al. | 514/12 |

OTHER PUBLICATIONS

Merrifield, J. Am. Chem. Soc., vol. 85, 2149–2154, 1963.

Grossman et al., "Response to Analogues of Growth Hormone–Releasing Hormone in Normal Subjects, and in Growth–Hormone Deficient Children and Young Adults", *Clinical Endocrinology; 21*, 321–324 (1984).

*Primary Examiner*—F. T. Moezie
*Attorney, Agent, or Firm*—Estelle J. Tsevdos; James F. Haley, Jr.; Douglas J. Gilbert

[57] ABSTRACT

The present invention relates to novel growth hormone-releasing peptides and method for increasing the release of growth hormone levels in mammals, as well as method for increasing milk production in dairy cows and increasing growth rates of animals, such as cattle, sheep, swine, and others. The novel peptides of this invention surprisingly are effective for releasing growth hormone levels in animals by replacing the natural amino acids in positions 1, 2, 3, 8, 9, 10, 12, 21 and 27, as well as derivatizing the N-terminal amino acid residue in human pancreatic islet tumor origin growth hormone-releasing factor.

53 Claims, No Drawings

GROWTH HORMONE-RELEASING PEPTIDES AND METHOD OF TREATING ANIMALS, THEREWITH

This application is a continuation-in-part of application Ser. No. 692,082, filed Jan. 17, 1985, which is a continuation-in-part of application Ser. No. 605,520, filed Apr. 30, 1984, now abandoned, which is a continuation-in-part of application Ser. No 522,067, filed Aug. 10, 1983, now abandoned.

The present invention relates to novel growth hormone-releasing peptides and method for increasing the release of growth hormone levels in animals, including mammals, therewith. Further, methods for increasing milk production in dairy cows result when the novel growth hormone-releasing peptides of the present invention are administered to those cows.

Recently, growth hormone-releasing factors (GRF) of human pancreatic islet tumor origin (hpGRF) were isolated, characterized, and shwon to possess growh hormone(GH)-releasing activity in rat anterior pituitary in vitro and in vivo by (1) Guillemin, P. Brazeau, P Böhlen, F. Esch, N. Ling, and W. B. Wehrenberg [Science, 218, 585 (1982)] and (2) J. Spiess, J. Rivier, M. Thornet, and W. Vale [Biochemistry, 21, 6037 (1082)]. Further, a synthetic hp GRF(]-29)-NH$_2$, an amidated fragment of the natural hp GRF(1-29)-NH$_2$, an amidated fragment of the natural hp GRF, was reported to possess full intrinsic biological activity by Spiess et al. of reference (2).

Since these hpGRF peptides contain 29 to 44 amino acid units with their molecular weights ranging from 3,085 to 5,035 Daltons, it is desirable to increase their potency so that the dosages administered for practical purpose could be reduced for eliciting the release of suitable levels of GH in mammals. It is, therefore, an object of the present invention to provide more potent peptides which mimic hpGRF and are effective for increasing the release of growth hormone to suitable levels in mammals.

Surprisingly, this objective is achieved by replacing the natural amino acids in positions 1, 2, 3, 8, 9, 10, 12, 21 and 27, as well as derivatizing the N-terminal amino acid residue in hpGRF 1 to 29, 1 to 40 and 1 to 44 as expressed below by the structural formulas (I), (II), and (III) respectively. These achievements are unexpected especially in view of reports by N. Ling and P. Brazeau [The Endocrine Society Program and Abstracts, 65th Annual Meeting, No. 295, Jun. 8 to 10, 1983, at San Antonio, Tex.] which indicate that AC-Tyr[1] and D-Tyr[1] hpGRF analogs have low potency with respect to the natural peptide, and by J. Rivier et al. [Abstract 8th American Peptide Symposium, May 22-27, 1983, paper 10-B], who indicated for hpGRF (1-27) that "some manipulation of the Tyr residue is compatible as long as a free amino terminus is conserved."

DESCRIPTION OF THE INVENTION

The polypeptides of the present invent ion are depicted by the structures of formulas (I), (II), and (III) below:

AMINO ACID SEQUENCE IN DESIGNATED PEPTIDES

HPGRF (1-44)NH$_2$
(Guillemin)

Tyr—Ala—Asp—Ala—Ile—Phe—Thr—Asn—Ser—Tyr—Arg—Lys—Val—Leu—Gly—Gln—Leu—Ser—Ala—Arg—
1

Lys—Leu—Leu—Gln—Asp—Il3—Met—Ser—Arg—Gln—Gln—Gly—Glu—Ser—Asn—Gln—Glu—Arg—Gly—Ala—
29

Arg—Ala—Arg—Leu—NH$_2$;
44 hpGRF (1-40)
(Vale)

Tyr—Ala—Asp—Ala—Ile—Phe—Thr—Asn—Ser—Tyr—Arg—Lys—Val—Leu—Gly—Gln—Leu—Ser—Ala—Arg—
1

Lys—Leu—Leu—Gln—Asp—Ile—Met—Ser—Arg—Gln—Gln—Gly—Glu—Ser—Asn—Gln—Glu—Arg—Gly—Ala;
29                                                                                              40 hpGRF (1-29)NH$_2$

Tyr—Ala—Asp—Ala—Ile—Phe—Thr—Asn—Ser—Tyr—Arg—Lys—Val—Leu—Gly—Gln—Leu—Ser—Ala—Arg—
1

Lys—Leu—Leu—Gln—Asp—Ile—Met—Ser—Arg—NH$_2$.
29

Code for L-Amino Acid, per IUPAC-IUB Commission on Biochemical Nomenclature:
Biochemistry 11, 1726-1732 (1972)

| | | | |
|---|---|---|---|
| His = Histidine | Val = Valine | Tyr = Tyrosine | Gln = Glutamine |
| Ser = Serine | Phe = Phenylalanine | Arg = Arginine | Met = Methionine |
| Asp = Aspartic Acid | Thr = Threonine | Leu = Leucine | Ile = Isoleucine |
| Ala = Alanine | Asn = Asparagine | Lys = Lysine | Glu = Glutamic Acid |
| Gly = Glycine | | Nle = Norleucine | |

R¹—A—B—C—Ala—Ile—Phe—Thr—X—Q—Z—Arg—U—Val—Leu— (I)
1                                10

Gly—Gln—Leu—Ser—Ala—Arg—W—Leu—Leu—Gln—Asp—Ile—Y—
                        20

Ser—Arg—R²
29

R¹—A—B—C—Ala—Ile—Phe—Thr—X—Q—Z—Arg—U—Val—Leu— (II)
1

Gly—Gln—Leu—Ser—Ala—Arg—W—Leu—Leu—Glu—Asp—Ile—Y—

Ser—Arg—Gln—Gln—Gly—Glu—Ser—Asn—Gln—Glu—Arg—Gly—Ala—R²
29                                                  40

R¹—A—B—C—Ala—Ile—Phe—Thr—X—Q—Z—Arg—U—Val—Leu— (III)
1

Gly—Gln—Leu—Ser—Ala—Arg—W—Leu—Leu—Gln—Asp—Ile—Y—

Ser—Arg—Gln—Gln—Gly—Glu—Ser—Asn—Gln—Glu—Arg—Gly—Ala—
29

Arg—Ala—Arg—Leu—R²
44

Wherein R¹ is hydrogen or $C_1$-$C_6$ straight- or branched-chain alkanoyl; R² is NR³R⁴ or OR³, wherein R³ and R⁴ are selected from the group consisting of hydrogen and a straight- or branched-chain alkyl group containing 1–6 carbon atoms; A represents a member selected from tyrosyl, D-tyrosyl, histidyl, D-histidyl, phenylalanyl, D-phenylalanyl, 4-chlorophenylalanyl, D-4-chlorophenylalanyl, 4-bromophenylalanyl, D-4-bromophenylalanyl, 4-fluorophenylalanyl, D-4-fluorophenylalanyl, 4-methoxyphenylalanyl, D-4-methoxyphenylalanyl, 4-benzyloxyphenylalanyl, D-4-benzyloxyphenylalanyl, tryptophyl, D-tryptophyl, 5-fluorotryptophyl, D-5-fluorotryptophyl, 5-chlorotryptophyl, D-5-chlorotryptophyl, 5-bromotryptophyl, D-5-bromotryptophyl, 5-methoxytryptophyl, D-5-methoxytryptophyl, 5-methyltryptophyl, or D-5-methyltryptophyl or

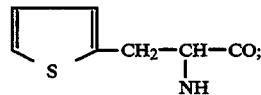

B represents a member selected from alanyl, D-alanyl, N-methylalanyl, N-methyl-D-alanyl, leucyl, D-leucyl, phenylalanyl, D-phenylalanyl, 4-chlorophenylalanyl, D-4-chlorophenylalanyl, 4-bromophenylalanyl, D-4-bromophenylananyl, 4-fluorophenylalanyl, D-4-fluorophenylalanyl, 4-methoxyphenylalanyl, D-4-methoxyphenylalanyl, 4-benzyloxyphenylalanyl, D-4-benzyloxyphenylalanyl, tryptophyl, D-tryptophyl, 5-fluorotryptophyl, D-5-fluorotryptophyl, 5-chlorotryptophyl, D-5-chlorotryptophyl, 5-bromtryptophyl, D-5-bromotryptophyl, 5-methoxytryptophyl, D-5-methoxytryptophyl or

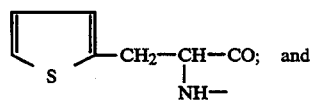

C represents a member selected from aspartyl, D-aspartyl, glutamyl and D-glutamyl; Q is seryl or D-seryl; X is asparaginyl or D-asparginyl; Y is norleucyl or methionyl, Z is tyrosyl or D-tyrosyl; U is lysyl or arginyl; and W is lysyl or arginyl; with the provisos that when R¹ is hydrogen and B is alanyl and C is aspartyl, and X is asparaginyl, and Q is seryl, and U and W are lysyl, and Z is tyrosyl, and Y is methionyl, A cannot be tyrosyl in Formula (I), (II) or (III); and when R¹ is hydrogen or alkanoyl and B is alanyl and C is aspartyl, and X is asparaginyl, and Q is seryl, and U and W are lysyl, and Z is tyrosyl, and Y is methionyl, A cannot be phenylalanyl, tryptophyl, histidyl, or D-tyrosyl in Formula (II) or (III); and further provided that where U is lysyl, W is lysyl and when U is arginyl, W is arginyl; and when B is N-methylalanyl or N-methyl-D-alanyl, U and W are arginyl; and the pharmaceutically acceptable salts thereof.

Preferred compounds of the invention are represented by Formulas (I) (II), or (III) wherein R¹, R², R³, and R⁴ are as described above; and A is selected from tyrosyl, D-tyrosyl, histidyl, D-histidyl; B is selected from alanyl, D-alanyl, N-methylalanyl, N-methyl-D-alanyl, leucyl, D-leucyl; C is selected from aspartyl, D-aspartyl, glutamyl and D-glutamyl; Q is seryl or D-seryl; X is selected from asparaginyl or D-asparaginyl; Y is selected from norleucyl or methionyl; U is lysyl or arginyl; and W is lysyl or arginyl; Z is tyrosyl or D-tyrosyl; with the above-mentioned provisos; and the pharmaceutically acceptable salts thereof.

Another preferred group of compounds of the invention have the Formula (I) configuration, wherein R¹ is seleted from hydrogen or $C_1$-$C_3$ alkanoyl; R² is NR³R⁴; R³ and R⁴ are each selected from hydrogen and $C_1$-$C_3$ alkyl; A is selected from tyrosyl, D-tyrosyl or histidyl; B is alanyl or D-alanyl; C is aspartyl or D-aspartyl; Q is seryl or D-seryl; U is lysyl or arginyl; W is lysyl or arginyl; X is asparaginyl or D-asparaginyl; Y is norleucyl or methionyl, and Z is tyrosyl or D-tyrosyl; with the above-mentioned provisos; and the pharmaceutically acceptable salts thereof.

The most preferred group of compounds of the invention have the formula (I) configuration, wherein R¹ is selected from hydrogen or acetyl. R² is NH₂; A is selected from tyrosyl, D-tyrosyl or histidyl; B is alanyl or D-alanyl; C is aspartyl or D-aspartyl; Q is seryl or D-seryl; U is lysyl or arginyl; W is lysyl or arginyl; X is asparaginyl or D-asparaginyl; and Y is norleucyl or methionyl, and Z is tyrosyl or D-tyrosyl; with the above-mentioned provisos; and pharmaceutically acceptable salts thereof.

The term "pharmaceutically acceptable salts" as used herein refers to non-toxic alkali metal, alkaline earth metal, ammonium, organoammonium and metallic salts commonly used in the pharmaceutical industry. These salts include, but are not limited to, the sodium, potassium, lithium, calcium, magnesium, zinc, ammonium, and trimethylammonium salts which are prepared by methods well known in the art. The term also includes non-toxic acid addition salts such as hydrochloride, hydrobromide, acetate, phosphate, sulfate, citrate, laurate, stearate, palmoate, and oleate, but are not limited to them. These acid addition salts are also prepared by methods well known in the art.

Further, the term "organoammonium" is defined as a group consisting of a positively charged nitrogen atom joined to from one to four aliphatic groups, each containing from one to 20 carbon atoms. Among the organic ammonium groups which are illustrative for the preparation of the aliphatic ammonium salts of this invention are: monoalkylammonium, dialkylammonium, trialkylammonium, tetraalkylammonium, monoalkenylammonium, dialkenylammonium, trialkenylammonium, monoalkynylammonium, dialkynylammonium, trialkanolammonium, $C_5$–$C_6$ cycloalkylammonium, piperidinium, morpholinium, pyrrolidinium, benzylammonium, and equivalents thereof.

In keeping with the standard nomenclature, abreviations for chiral amino acid residues used in the present specification and claims are as follows:

| Abbreviation | Name |
| --- | --- |
| His | L-histidyl |
| Ser | L-seryl |
| D-Ser | D-Seryl |
| Asp | L-aspartyl |
| D-Asp | D-aspartyl |
| Ala | L-alanyl |
| D-Ala | D-alanyl |
| Val | L-valinyl |
| Phe | L-phenylalanyl |
| Thr | L-threonyl |
| Asn | L-asparaginyl |
| D-Asn | D-asparaginyl |
| Tyr | L-tyrosyl |
| Arg | L-arginyl |
| Leu | L-leucyl |
| D-Leu | D-leucyl |
| Nle | L-norleucyl |
| Lys | L-lysyl |
| Gln | L-glutaminyl |
| Met | L-methionyl |
| Ile | L-isoleucyl |
| Glu | L-glutamyl |
| D-Glu | D-glutamyl |
| D-Tyr | D-tyrosyl |
| D-His | D-histidyl |
| D-Phe | D-phenylalanyl |
| (4-Cl)Phe | L-4-chlorophenylalanyl |
| D-(4-Cl)Phe | D-4-chlorophenylalanyl |
| (4-Br)Phe | L-4-bromophenylalanyl |
| D-(4-Br)Phe | D-4-bromophenylalanyl |
| (4-F)Phe | L-4-fluorophenylalanyl |
| D-(4-F)Phe | D-4-fluorophenylalanyl |
| (4-MeO)Phe | L-4-methoxyphenylalanyl |
| D-(4-MeO)Phe | D-4-methoxyphenylalanyl |
| (4-ϕCH$_2$O)Phe | L-4-benzloxyphenylalanyl |
| D-(4-OCH$_2$ϕ)Phe | D-4-benzloxyphenylalanyl |
| Trp | L-tryptophyl |
| D-Trp | D-tryptophyl |
| (5-F)Trp | L-5-fluorotryptophyl |
| D-(5-F)Trp | D-5-fluorotryptophyl |
| (5-Cl)Trp | L-5-chlorotryptophyl |
| D-(5-Cl)Trp | D-5-chlorotryptophyl |
| (5-Br)Trp | L-5-bromotryptophyl |
| D-(5-Br)Trp | D-5-bromotryptophyl |
| (5-MeO)Trp | L-5-methoxytryptophyl |
| D-(5-MeO)Trp | D-5-methoxytryptophyl |
| (5-Me)Trp | L-5-methyltryptophyl |
| D-(5-Me)Trp | D-5-methyltryptophyl |

Unless otherwise specified, the amino acid residues that are named herein without the prefix L will refer to the naturally occurring absolute configuration L. The $R^1$ group refers to the substituent on the N-terminus amino acid (position 1 of the peptide according to standard nomenclature.

Other abbreviations used in the present specification are:

| | |
| --- | --- |
| Fmoc = | fluorenylmethyloxycarbonyl |
| Boc = | t-butyloxycarbonyl |
| Tos = | p-toluenesulfonyl |
| hplc = | high performance liquid chromatography |
| tlc = | thin-layer chromatography |
| TFA = | trifluoroacetic acid |
| Ac = | acetyl |
| Z = | benzyloxycarbonyl |

Solid-phase synthesis of the Formulas (I), (II), and (III) peptides can be carried out on a Beckman 990 automatic peptide synthesizer. Preparative HPLC can be performed on a thick-walled glass column (2.5×45 cm) containing Whatman LRP-1 reverse phase packing ($C_{18}$ silica 13–22 μm) pumped with Fluid Metering Company pump and pulse damper. Amino acid analyses can be run on a Beckman 119 CL analyzer and processed with a System AA computing integrator.

Amino acid derivatives utilized in the preparation of the compounds of the present invention are available from several chemical supply houses including: Bachem, Inc., Torrance, Calif., and Chemical Dyanamics, Inc., Plainfield, N.J.

The peptides having the Formulas (I), (II), and (III) configurations can be conveniently prepared by standard solid-phase techniques; for example, the C-terminal protected amino acid can be attached to a chloromethyl resin, a hydroxymethyl resin, a benzhydrylamine (BHA) resin or a p-methylbenzylhydrylamine (p-Me-BHA) resin. One such chloromethyl resin is sold under the trade name Bio-Beads SX-1 by Bio Rad Laboratories, Richmond, Calif. The preparation of the hydroxymethyl resin is described by Bodansky et al., Chem. Ind. (London) 38, 1597 (1966). The BHA resin has been described by Pietta and Marshall, Chem. Commun. 650 (1970) and commercially available from Bachem, Inc. Torrance, Calif.

According to an embodiment of the invention, the peptides of Formulas (I), (II), and (III) are prepared by means of solid-phase peptide synthesis by standard procedures, although it may also be prepared by treatment of the peptide-resin with ammonia to give the desired side-chain protected amide or with an alkylamine to give a side-chain protected alkylamide or dialkylamide.

The α-amino protecting group is Fmoc for the amino acid in position one, and the side-chain protecting group is Boc instead of Z for the appropriate preceeding amino acid, when the chloromethyl or hydroxymethyl resin is used.

Side-chain protection can then be removed in the usual fashion by treatment with HF to give the free peptide amides, alkylamides, or dialkylamides.

In preparing the esters of this invention, the resins used to prepare the acids of Formulas (I), (II), and (III) ($R^2$=OH) can be employed, and the side-chain protected peptide can be cleaved with a base and appropriate alcohol, i.e., methanol. Side-chain protecting groups can then be removed in the usual fashion by treatment with HF to obtain the desired ester.

The solid-phase procedure discussed above is well known in the art and has been essentially described by Stewart and Young, *Solid Phase Peptide Synthesis*, Freeman and Company, San Francisco, Calif. (1969).

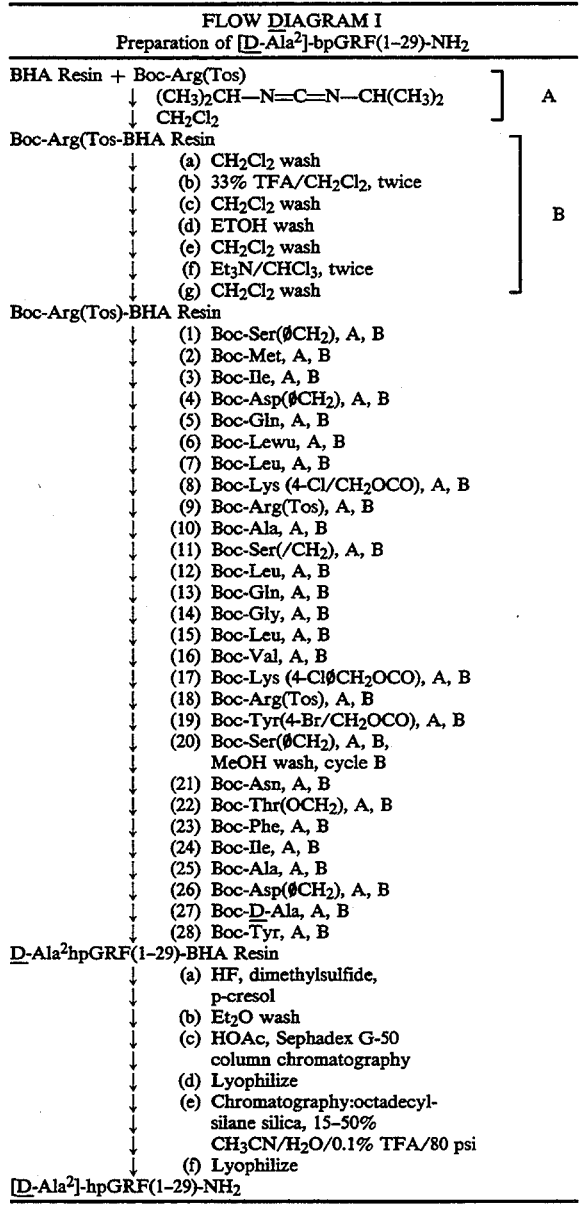

To prepare formula (II) analogs, the C-terminal protected amino acid Boc-alanine is attached to the desired resin as described for preparing formula (I) peptides; likewise to prepare formula (III) analogs, the C-terminal protected amino acid Boc-leucine is attached to the desired resin. The subsequent amino acid groups are then sequentially coupled to the solid phase in the manner described in Flow Diagram I.

To prepare a N-terminal alkanoyl [$R^1$ of (I), (II), and (III)] peptide, the peptide bonded to the resin is allowed to stir in 5 to 20% solutions of the appropriate acid anhydride in $CH_2Cl_2$ containing triethylamine or other standard acid accepting bases for 20 to 120 minutes at room temperature. Subsequently, the standard reagents for cleaving the peptide from the resin is used to obtain the desired peptide of formulas (I), (II), or (III).

Thus, by the above-mentioned procedure, the following peptides are prepared:
[N-Acetyl]-hpGRF(1–29)-$NH_2$
[D-$Tyr^1$]-hpGRF(1–29)-$NH_2$
[N-Acetyl-D-$Thr^1$]-hpGRF(1–29)-$NH_2$
[N-Acetyl-D-$Ala^2$]-hpGRF(1–29)-$NH_2$
[D-$Asp^3$]-hpGRF(1–29)-$NH_2$
[N-Acetyl-D-$Asp^3$]-hpGRF(1–29)-$NH_2$
[D-$Tyr^1$,D-$Ala^2$]hpGRF(1–29)-$NH_2$
[N-Acetyl-D-$Tyr^1$,D-$Ala^2$]-hpGRF(1–29)-$NH_2$
[$His^1$,D-$Ala^2$]-hpGRF(1–29)-$NH_2$
[N-Acetyl-$His^1$,D-$Ala^2$]-hpGRF(1–29)-$NH_2$
[D-$Tyr^1$,D-$Ala^2$,D-$Asp^3$]-hpGRF(1–29)-$NH_2$
[N-Acetyl-D-$Tyr^1$,D-$Ala^2$,D-$Asp^3$]-hpGRF(1–29)-$NH_2$
[$His^1$,D-$Ala^2$,D-$Asp^3$]-hpGRF(1–29)-$NH_2$
[N-Acetyl-$His^1$,D-$Ala^2$,D-$Asp^3$]-hpGRF(1–29)-$NH_2$
[$Phe^1$]-hpGRF(1–29)-$NH_2$
[N-Acetyl-$His^1$,D-$Ala^2$,$Nle^{27}$]-hpGRF(1–29)-$NH_2$
[N-Acetyl-$Phe^1$]-hpGRF(1–29)-$NH_2$
[D-$Tyr^{10}$]-hpGRF(1–29)-$NH_2$
[D-$Ala^2$,D-$Tyr^{10}$]-hpGRF(1–29)-$NH_2$
[D-$Ser^9$]-hpGRF(1–29)-$NH_2$
[D-$Asn^8$]-hpGRF(1–29)-$NH_2$
[D-$Ala^2$,$Nle^{27}$]-hpGRF(1–29)-$NH_2$
[$His^1$,D-$Ala^2$,$Nle^{27}$]-hpGRF(1–29)-$NH_2$
[D-$Ala^2$,D-$Asn^8$,$Nle^{27}$]-hpGRF(1–29)-$NH_2$
[D-$Asp^3$,D-$Asn^8$,$Nle^{27}$]-hpGRF(1–29)-$NH_2$
[D-$Ala^2$,D-$Asp^3$,D-$Asn^8$,$Nle^{27}$]-hpGRF(1–29)-$NH_2$
[D-$Phe^1$]-hpGRF(1–29)-$NH_2$
[N-Acetyl-D-$Phe^1$]-hpGRF(1–29)-$NH_2$
[D-$His^1$]-hpGRF(1–29)-$NH_2$
[N-Acetyl-D-$His^1$]-hpGRF(1–29)-$NH_2$
[D-$Leu^2$]-hpGRF(1–29)-$NH_2$
[N-Acetyl,D-$Leu^2$]-hpGRF(1–29)-$NH_2$
[D-$Phe^2$]-hpGRF(1–29)-$NH_2$
[N-Acetyl,D-$Phe^2$]-hpGRF(1–29)-$NH_2$
[$Asp^3$]-hpGRF(1–29)-$NH_2$
[N-Acetyl,$Asp^3$]-hpGRF(1–29)-$NH_2$
[D-$Glu^3$]-hpGRF(1–29)-$NH_2$
[N-Acetyl,D-$Glu^3$]-hpGRF(1–29)-$NH_2$
[$Arg^{12,21}$]-hpGRF(1–29)-$NH_2$
[N-Acetyl,$Tyr^1$,$Arg^{12,21}$]-hpGRF(1–29)-$NH_2$
[D-$Ala^2$,$Arg^{12,21}$]-hpGRF(1–29)-$NH_2$
[D-$Ala^2$,$Arg^{12,21}$]-hpGRF(1–40)-$NH_2$
[N-Acetyl,D-$Ala^2$,$Arg^{12,21}$]-hpGRF(1–40)-$NH_2$
[D-$Ala^2$,$Arg^{12,21}$]-hpGRF(1–44)-$NH_2$
[N-Acetyl,$Agr^{12,21}$]-hpGRF(1–44)-$NH_2$
[D-$Ala^2$]-hpGRF(1–40)-$NH_2$
[D-$Ala^2$]-hpGRF(1–44)-$NH_2$
[N-Acetyl,D-$Ala^2$]-hpGRF(1–40)-$NH_2$
[N-Acetyl,D-$Ala^2$]-hpGRF(1–44)-$NH_2$ Accordingly, the present invention includes pharmaceutical compositions comprising at least one of the peptides of formulas (I), (II), or (III) as an active ingredient, in association with a pharmaceutical carrier or diluent for use in stimulating growth-hormone release in mammals as follows:

R$^1$-A-B-C-Ala-Ile-Phe-Thr-X-Q-Z-Arg-U-Val-Leu-Gly-Gln-Leu-Ser-Ala-Arg-W-Leu-Leu-Gln-Asp-Ile-Y-Ser-Arg-R$_2$  (I)

or

R$^1$-A-B-C-Ala-Ile-Phe-Thr-X-Q-Z-Arg-U-Val-Leu-Gly-Gln-Leu-Ser-Ala-Arg-W-Leu-Leu-Gln-Asp-Ile-Y-Ser-Arg-Gln-Gln-Gly-Glu-Ser-Asn-Gln-Glu-Arg-Gly-Ala-R$^2$  (II)

or

R$^1$-A-B-C-Ala-Ile-Phe-Thr-X-Q-Z-Arg-U-VAL-Leu-Gly-Gln-Leu-Ser-Ala-Arg-W-Leu-Leu-Gln-Asp-Ile-Y-Ser-Arg-Gln-Gln-Gly-Glu-Ser-Asn-Gln-Glu-Arg-Gly-Ala-Arg-Ala-Arg-Leu-R$^1$  (III)

wherein R$^1$ is hydrogen or C$_1$–C$_6$ straight- or branched-chain alkanoyl; R$^2$ is NR$^3$R$^4$ or OR$^3$; R$^3$ and R$^4$ are selected from the group consisting of hydrogen and a straight- or branched-chain alkyl group containing one to six carbon atoms; A represents a member selected from tyrosyl, D-tyrosyl, histidyl, D-histidyl, phenylalanyl, D-phenylalanyl, 4-chlorophenylalanyl, D-4-chlorophenylalanyl, 4-bromophenylalanyl, D-4-bromoalanyl, 4-fluorophenylalanyl, D-4-fluorophenylalanyl, 4-methoxyphenylalanyl, D-4-methoxyphenylalanyl, 4-benzyloxyphenylalanyl, D-4-benzyloxyphenylalanyl, trytophyl, D-tryptophyl, 5-fluorotryptophyl, D-5-fluorotryptophyl, 5-chlorotryptophyl, D-5-chlorotryptophyl, 5-bromotryptophyl, D-5-bromotryptophyl, 5-methoxytryptophyl, D-5-methoxytryptophyl, 5-methyltryptophyl, D-5-methyltryptophyl or

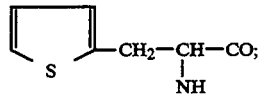

B represents a member select ed from alanyl, D-alanyl, N-methylalanyl, N-methyl-D-alanyl, leucyl, D-leucyl, phenylalanyl, D-phenylalanyl, 4-chlorophenylalanyl, D-4-chlorophenylalanyl, 4-bromophenylalanyl, D-4-bromophenylalanyl, 4-fluorophenylalanyl, D-4-fluorophenylalanyl, 4-methoxyphenylalanyl, D-4-methoxyphenylalanyl, 4-benzyloxyphenylalanyl, D-4-benzyloxyphenylalanyl, tryptophyl, D-tryptophyl, 5-fluorotryptophyl, D-5-fluorotryptophyl, 5-chlorotryptophyl, D-5-chlorotryptophyl, 5-bromotryptophyl, D-5-bromotryptophyl, 5-methoxytryptophyl, D-5-methoxytryptophyl or

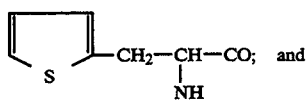

C represents a member selected from aspartyl, D-aspartyl, glutamyl and D-glutamyl; Q is seryl or D-seryl; X represents asparaginyl or D-asparaginyl; Y represents norleucyl or methionyl, and Z is tyrosyl or D-tyrosyl; U is lysyl or arginyl; and W is lysyl or arginyl; with the provisos that when R$^1$ is hydrogen, B is alanyl, and C is aspartyl, and X is asparaginyl, and Q is seryl, and Z is tyrosyl, and Y is methionyl, A cannot be tyrosyl in Formulas (I), (II), and (III) or phenylalanyl, tryptophyl, histidyl or D-tyrosyl in Formulas (II) and (III); and when U is lysyl, W is lysyl; and when U is arginyl, W is arginyl, and when B is N-methylalanyl or N-methyl-D-alanyl, U and W are arginyl; and the pharmaceutically acceptable salts thereof.

In practice, it has been found that the Formulas (I), (II), and (III) compounds of the present invention are effective for increasing the release of growth hormone in mammals when administered thereto in an amount sufficient to provide said-treated mammals with from 0.000001 to 0.1 mg/kg of mammalian body weight/day of said Formulas (I), (II), or (III) compound.

Preferred peptides for increasing release of growth hormone in mammals have a structure selected from Formulas (I), (II), or (III) above, wherein R$^1$, R$^2$, R$^3$, and R$^4$ are selected from those described above; A is tyrosyl, D-tyrosyl, histidyl, D-histidyl; B is alanyl, D-alanyl, leucyl, D-leucyl; C is aspartyl, D-aspartyl, glutamyl, or D-glutamyl; Q is seryl or D-seryl; X is asparaginyl or D-asparginyl; Y is norleucyl or methionyl, and Z is tyrosyl or D-tyrosyl; with the above-mentioned provisos; and the pharmaceutically acceptable salts thereof.

Another preferred group of compounds of the present invention effective for increasing growth hormone-release in mammals have the structure illustrated by Formula (I) wherein R$^1$ is hydrogen or C$_1$–C$_3$ alkanoyl; R$^2$ is NR$^3$R$^4$; R$^3$ and R$^4$ are each hydrogen or a straight- or branched-chain or C$_1$–C$_3$ alkyl; A is tyrosyl, D-tyrosyl, or histidyl; B is alanyl or D-alanyl; C is aspartyl or D-aspartyl; Q is seryl or D-seryl; U is lysyl or arginyl; W is lysyl or arginyl; X is asparaginyl or D-asparginyl; Y is norleucyl or methionyl, and Z is tyrosyl or D-tyrosyl; with the above-mentioned provisos; and the pharmaceutically acceptable salts thereof.

The most preferred group of compounds of the invention have the Formula (I) configuration, wherein R$^1$ is selected from hydrogen or acetyl; R$^2$ is NH$_2$; A is selected from tyrosyl, D-tyrsyl or histidyl; B is alanyl or D-alanyl; C is aspartyl or D-aspartyl; Q is seryl or R-seryl; U is lysyl or arginyl; W is lysyl or arginyl; X is asparaginyl or D-asparaginyl; and Y is norleucyl or methionyl; with the above-mentioned provisos; and the pharmaceutically acceptable salts thereof.

These peptides are useful for treatments of symptoms related to growth hormone deficiencies, for increasing wool growth, for increasing rate of growth of meat-producing animals, for improving carcass quality in meat-producing animals (i.e., more protein and less fat), for improving feed efficiency in meat-producing animals and dairy cows, for increasing milk production in dairy herds, and in healing wounds.

In order to facilitate a further understanding of the invention, the following examples are presented primarily for the purpose of illustrating certain more specific details thereof. The invention is not to be deemed limited thereby except as defined in the claims.

EXAMPLE 1

Protected Human Pancreatic Growth Hormone-Releasing Factor(9–29)-Benzhydrylamine Resin Benzhydrylamine polystyrene resin (commercially available from Bachem, Inc., Torrance, Calif.) (6.0 g, 3.00 mmol) in the chloride ion form is placed in the reaction vessel of a Beckman 990 automatic peptide synthesizer programmed to carry out the following work-wash cycle: (a) $CH_2Cl_2$; (b) 33% trifluoroacetic acid in $CH_2Cl_2$ (two times for one and 25 minutes each ); (c) $CH_2Cl_2$; (d) $C_2H_5OH$; (e) $CH_2Cl_2$; (f) 10% $(C_2H_5)_3N$ in $CHCl_3$ (two times for two minutes each); and (g) $CH_2Cl_2$.

The neutralized resin is stirred with t-butyl-oxycarbonyl(Boc)-N-tosyl-1-arginine [Boc-Arg(Tos)] and diisopropylcarbodiimide (6 mmol) in $CH_2Cl_2$ for one hour, and the resulting amino acid resin is then cycled through the steps (a) through (g) in the above wash program. The following L-amino acids (3 mmol) are then coupled successively by the same reaction cycle: Boc-Ser(benzyl), Boc-Met, Boc-Ile, Boc-Asp(benzyl), Boc-Gln, Boc-Leu, Boc-Leu, Boc-Lys(-4-chlorocarbenzoxy), Boc-Arg(Tos), Boc-Ala, Boc-Ser(benzyl), Boc-Leu, Boc-Gln, Boc-Gly, Boc-Leu, Boc-Val, Boc-Lys(4-chlorocarbenzoxy), Boc-Arg(tosyl), Boc-Tyr(4-bromocarbenzoxy) and Boc-Ser(benzyl), except that Boc-Gln is coupled in the presence of 1-hydroxybenzotriazole (6 mmol) in dimethylformamide solution.

The completed peptide-benzhydrylamine resin, with the N-terminal Boc group removed, is then washed with $CH_3OH$ and air dried to give 11.79 g of material.

EXAMPLE 2

Preparation of Protected D-tyrosine-1-Human Pancreatic-Growth Hormone-Releasing Factor (1–29)-Benzhydrylamine Resin Peptide benzhydrylamine resin (0.98 g, 0.25 mmol) containing the 9–29 residues of the peptide as described in Example 1 is subjected to the work-wash cycle also described in Example 1. The neutralized resin is stirred with Boc-L-asparagine (0.75 mmol), diisopropylcarbodiimide (0.75 mmol), and 1-hydroxybenzotriazole (0.75 mmol) in dimethylformamide.

The following amino acid derivatives (0.75 mmol) are then coupled successively by the same treatment cycle described in Example 1: Boc-Thr(benzyl), Boc-Phe, Boc-Ile, Boc-Ala, Boc-Asp(benzyl), Boc-Ala, and Boc-D-Tyr. The completed 1–29 peptide resin is then cycled through the standard work-wash program described in Example 1 in order to remove the N-terminal Boc group.

EXAMPLE 3

Preparation of D-tyrosine-1-Human Pancreatic Growth Hormone-Releasing(1–29)-Amide [(D-Tyr$^1$)-hpGRF(1–29)-NH$_2$]

A mixture of the 1–29 peptide resin described in Example 2 (0.75 mmol) and a solution of hydrogen fluoride (10 mL), dimethylsulfide (26 mL), and p-cresol (4 mL) are stirred at 0° C. for 75 minutes. Excess reagents are then rapidly evaporated under a stream of dry nitrogen and hydrogen fluoride (35 mL) is added, and the mixture stirred for a further 45 minutes at 0° C. Excess hydrogen fluoride is evaporated under nitrogen, and the resin plus free peptide are washed free of p-cresol with a large volume of diethyl ether.

The peptide is extracted into 50% acetic acid solution and applied to a column (2.5×95 cm) of Sephadex G-50 which is eluted with 2M acetic acid. Eluant is monitored at 280 nM and fractions containing a major uv-absorbing peak are pooled and lyophilized. A solution of the lyophilized powder is eluted on a column (1.5×45 cm) of octadecylsilane silica having a mesh size of 15–20M and pore size of 300 A° (purchased from Vydac, Hesperia, Calif.). A linear elution gradient of 15–50% acetonitrile in 0.1% trifluoroacetic acid solution is employed at a pumping pressure of about 80 psi. Emerging fractions are monitored at 280 nm and are each examined by analytical hplc at a wave length of 215 nm in order to ensure maximum homogeneity of pooled fractions. Lyophilization of these gave the title peptide as a white powder (32 mg).

This material gives one peak emerging at 38 minutes using analytical hplc on a column (0.4×25 cm) of Vydac octadecylsilane silica (5M mesh size, 300 A°) which is pumped at 2 mL/min with a linear gradient of 20 to 40% acetonitrile in 0.1% trifluoracetic acid. Tlc on silica gel using the solvent system 1-butanol: pyridine: acetic acid: water (15:10:3:12) gives one spot as visualized by chlorine-starch spray reagent. Amino acid analysis of a 6M HCl hydrolysate gives the following amino acid ratios: Asp, 3.08; Thr, 1.08; Ser, 3.01; Glu, 2.22; Gly, 1.10; Ala, 3.30; Val, 0.87; Met, 0.97; Ile, 1.69; Leu, 3.61; Tyr, 1.60; Phe, 1.05; Lys, 2.07; Arg, 3.28.

EXAMPLE 4

Preparation of Protected N-acetyl Human Pancreatic Growth Hormone-Releasing Factor(1–29)-Benzhydrylamine Resin Peptide-benzhydrylamine resin(9–29) (0.98 g, 0.25 mmol) prepared in Example 1 is subjected to the coupling cycles described in Example 2, except that L-Tyr is used in place of D-Tyr. The 1–29 peptide resin, with the N-terminal Boc group removed, is acetylated by stirring with a 10% solution of acetic anydride/Et$_3$N in methylene chloride (30 minutes).

EXAMPLE 5

Preparation of N-acetyl Human Pancreatic Growth Hormone-Releasing Factor(1–29)-Amide (N-acetyl-hpGRF(1–29)-NH$_2$)-

The peptide resin (0.75 mmol) described in Example 4 is treated with hydrogen fluoride mixtures and purified as described in Example 3. The lyophilized, purified peptide weighed 16.2 mg.

This material gives one peak emerging at 36.5 minutes using the analytical hplc conditions described in Example 3. Tlc using the conditions also described in Example 3 gives one spot. Amino acid analysis of a 6M HCl hydrolysate gives the following amino acid ratios: Asp, 3.05; Thr, 1.08; Ser, 2.96; Glu, 2.20; Gly, 1.20; Ala, 3.30; Val, 0.81; Met, 1.00; Ile, 1.65; Leu, 3.50; Tyr, 1.61.; Phe, 1.20; Lys, 2.10; Arg, 3.17.

EXAMPLE 6

Preparation of Protected D-alanine$^2$-human Pancreatic Growth Hormone-Releasing Factor(1–29)-Benzhydrylamine Resin Peptide-benzhydrylamine resin (0.98 g, 0.25 mmol) prepared in Example 1 is subjected to the coupling cycles described in Example 2, except that D-alanine is used in place of L-alanine in position 2 and L-tyrosine in place of D-tyrosine in position 1.

EXAMPLE 7

Preparation of D-alanine²-human Pancreatic Growth Hormone-Releasing(1–29)-amide [(D-Ala²)-hpGRF(1–29)-NH₂]

The peptide resin (0.25 mmol) described in Example 6 is treated with hydrogen fluoride mixtures and purified as described in Example 3. The purified, lyophilized peptide weighs 27.9 mg. This material gives one peak emerging at 35 minutes using the analytical hplc conditions as described in Example 3. Tlc using the conditions described in Example 3 gives one spot. Amino acid analysis of a 6M HCl hydrolysate gives the following amino acid ratios: Asp, 3.06; Thr, 1.07; Ser, 3.05; Glu, 2.19; Gly, 1.02; Ala, 3.29; Val, 0.94; Met, 1.10; Ile, 1.72; Leu, 3.66; Tyr, 1.62; Phe, 0.90; Lys, 2.97; Arg, 3.19.

EXAMPLE 8

Preparation of Protected D-aspartic Acid³-human Pancreatic Growth Hormone-Releasing Factor(1–29)-benzhydrylamine resin Peptide-benzhydrylamine resin (0.98 g, 0.25 mmol) prepared in Example 1 is subjected to the coupling cycles described in Example 2, except that D-aspartic acid is used in place of L-aspartic acid in position 3 and L-tyrosine in place of D-tyrosine in position 1.

EXAMPLE 9

Preparation of D-aspartic Acid³-human Pancreatic growth hormone-releasing(1–29)-amide [(D-Asp³)-hpGRF(1–29)-NH₂]

The peptide resin (0.25 mmol) described in Example 8 is treated with hydrogen fluoride mixtures and purified as described in Example 3. The purified, lyophilized peptide weighed 15.3 mg. This material gives one peak emerging at 34 minutes using the analytical hplc conditions as described in Example 3. Tlc using the conditions described in Example 3 gives one spot. Amino acid analysis of a 6M HCl hydrolysate gives the following amino acid ratios: Asp, 3.17; Thr, 1.22; Ser, 3.08; Glu, 2.36; Gly, 1.06; Ala, 3.30; Val, 0.96; Met, 0.84; Ile, 1.76; Leu, 3.71; Tyr, 1.00; Phe, 0.92; Lys, 2.21; Arg, 3.30.

EXAMPLE 10

Preparation of Protected N-acetyl-D-tyrosine¹,D-alanine²-human Pancreatic Growth Hormone-Releasing factor(1–29)-benzhydrylamine resin Peptide-benzhydrylamine resin (0.98-g, 0.25 mmol) prepared in Example 1 is subjected to the coupling cycles described in Example 2, except that D-alanine is used in place of L-alanine in position 2. and D-tyrosine in place of L-tyrosine in position 1.

EXAMPLE 11

Preparation of N-acetyl-D-tyrosine¹,D-alanine²-human pancreatic growth hormone-releasing (1–29)-amine [(N-acetyl-D-Tyr¹,D-Ala²)-hpGRF(1–29)-NH₂]

The peptide resin (0.25 mmol) described in Example 10 is treated with hydrogen fluoride mixtures and purified as described in Example 3. The purified, lyophilized peptide weighed 5 mg. This material gives one peak emerging at 33 minutes using the analytical hplc conditions as described in Example 3. Tlc using the conditions described in Example 3 gives one spot. Amino acid analysis of a 6M HCl hydrolysate gives the following amino acid ratios: Asp, 3.08; Thr, 1.08; Ser, 3.01; Glu, 2.22; Gly, 1.10; Ala, 3.30; Val, 0.87; Met, 0.97; Ile, 1.69; Leu, 3.61; Tyr, 1.60; Phe, 1.05; Lys, 2.07; Arg, 3.28.

EXAMPLE 12

Preparation of Protected N-acetyl-D-tyrosine¹,D-alanine²,D-aspartic Acid³-human Pancreatic Growth hormone-releasing factor (1–29)-benzhydrylamine resin Peptide-benzhydrylamine resin (0.98 g, 0.25 mmol) prepared in Example 1 is subjected to the coupling cycles described in Example 4, except that D-aspartic acid is used in place of L-aspartic acid in position 3, D-alanine in place of L-aspartic acid in position 2, and D-tryosine in place of L-tyrosine in position 1.

EXAMPLE 13

Preparation of N-acetyl-D-tyrosine¹,D-alanine²,D-aspartic acid³-human Pancreatic Growth Hormone-Releasing(1–29)-amine [(N-acetyl-D-Tyr¹,D-Ala²,D-Asp³)-hpGRF(1–29)-NH₂]

The peptide resin (0.25 mmol) described in Example 12 is treated with hydrogen fluoride mixtures and purified as described in Example 3. The purified, lyophilized peptide weighs 12 mg. This material gives one peak emerging at 34 minutes using the analytical hplc conditions as described in Example 3. Tlc using the conditions described in Example 3 gives one spot. Amino acid analysis of a 6M HCl hydrolysate gave the following amino acid ratios: Asp, 3.06; Thr, 1.07; Ser, 3.00; Glu, 2.18; Gly, 1.11; Ala, 3.30; Val, 0.82; Met, 0.97; Ile, 1.62; Leu, 3.43; Tyr, 1.69; Phe, 0.92; Lys, 2.03; Arg, 3.13.

EXAMPLE 14

Preparation of Protected N-acetyl-tosyl-L-histidine-1,D-alanine-2-human Pancreatic Growth Hormone-Releasing factor(1–29)-benzhydrylamine resin Peptide-benzhydrylamine resin (0.98 g, 0.25 mmol) prepared in Example 1 is subjected to the coupling cycles described in Example 4, except that D-alanine is used in place of L-alanine in position 2, and D-tosyl-histidine in place of L-tyrosine in position 1.

EXAMPLE 15

Preparation of N-acetyl-L-histidine-1,D-alanine²-human Pancreatic Growth Hormone-Releasing(1–29)-amine [(N-acetyl-His¹,D-Ala²)-hpGRF(1–29)-NH₂]

The peptide resin (0.25 mmol) described in Example 14 is treated with hydrogen fluoride mixtures and purified as described in Example 3. The purified, lyophilized peptide weighs 18 mg. This material gives one peak emerging at 31 minutes using the analytical hplc conditions as described in Example 3. Tlc using the conditions described in Example 3 gives one spot. Amino acid analysis of a 6M HCl hydrolysate gives the following amino acid ratios: Asp, 3.06; Thr, 1.01; Ser, 3.00; Glu, 2.26; Gly, 1.10; Ala, 3.30; Val, 0.79; Met, 0.97; Ile, 1.69; Leu, 3.71; Tyr, 0.81; Phe, 0.96; His, 0.95; Lys, 2.15; Arg, 3.30.

EXAMPLE 16

The following N-acyl ($R^1$) growth hormone-releasing factors(1–29) of structural Formula (I) are prepared by using the methods described in Example 4 and Example 5 by substituting the following acid anhydrides for acetic anhydride and the appropriate GRF(1–29), wherein $R^2$ is $NH_2$.

| Anhydride | $R^1$ | GRF(1–29) |
|---|---|---|
| HCO—O—COCH$_3$ | HCO | hp |
| (CH$_3$CH$_2$CO)$_2$O | CH$_3$CH$_2$CO | hp |
| [(CH$_3$)$_2$CH—CO]$_2$O | (CH$_3$)$_2$CHCO | hp |
| [CH$_3$(CH$_2$)$_4$CO]$_2$) | CH$_3$(CH$_2$)$_4$CO | hp |
| [(CH$_3$)$_3$CCO]$_2$O | (CH$_3$)$_3$CCO | [D-Ala$^2$]-hp |
| [(CH$_3$)$_2$CH—CO]$_2$O | (CH$_3$)$_2$CHCO | [D-Ala$^2$]-hp |
| [CH$_3$(CH$_2$)$_3$CO)$_2$O | CH$_3$(CH$_2$)$_3$CO | [D-Ala$^2$]-hp |
| (CH$_3$CO)$_2$O | CH$_3$CO | [D-Ala$^2$]-hp |
| [CH$_3$(CH$_2$)$_4$CO]$_2$O | CH$_3$(CH$_2$)$_4$CO | [D-Ala$^2$]-hp |
| HCO—O—COCH$_3$ | HCO | [D-Ala$^2$]-hp |
| CH$_3$(CH$_2$)$_2$CO | CH$_3$(CH$_2$)$_2$CO | [D-Ala$^2$]-hp |
| (CH$_3$CO)$_2$O | CH$_3$CO | [D-Asp$^3$]-hp |
| [CH$_3$(CH$_2$)$_4$CO]$_2$CO | CH$_3$(CH$_2$)$_4$CO | [D-Asp$^3$]-hp |
| (CH$_3$CH$_2$CO)$_2$O | CH$_3$CH$_2$CO | [His$^1$, D-Ala$^2$]-hp |
| [(CH$_3$)$_2$CHCO]$_2$O | (CH$_3$)$_2$CHCO | [His$^1$, D-Ala$^2$]-hp |
| CH$_3$(CH$_2$)$_4$CO | CH$_3$(CH$_2$)$_4$CO | [His$^1$, D-Ala$^2$]-hp |
| HCO—OCOCH$_3$ | HCO | [D-Tyr$^1$, D-Ala$^2$]-hp |
| (CH$_3$CH$_2$CO)$_2$O | CH$_3$CH$_2$CO | [D-Tyr$^1$, D-Ala$^2$]-hp |
| [(CH$_3$)$_2$CHCO]$_2$O | (CH$_3$)$_2$CHCO | [D-Tyr$^1$, D-Ala$^2$]-hp |
| [CH$_3$(CH$_2$)$_3$CO]$_2$O | CH$_3$(CH$_2$)$_3$CO | [D-Tyr$^1$, D-Ala$^2$]-hp |
| [CH$_3$(CH$_2$)$_4$CO]$_2$O | CH$_3$(CH$_2$)$_4$CO | [D-Tyr$^1$, D-Ala$^2$]-hp |
| [(CH$_3$)$_3$CCO]$_2$O | (CH$_3$)$_3$CCO | [D-Tyr$^1$, D-Ala$^2$]-hp |
| HCOOCH$_3$ | HCO | [D-Tyr$^1$, D-Ala$^2$, D-Asp$^3$]-hp |
| (CH$_3$CH$_2$CO)$_2$O | CH$_3$CH$_3$CO | [D-Tyr$^1$, D-Ala$^2$, D-Asp$^3$]-hp |
| [(CH$_3$)$_2$CHCO]$_2$O | (CH$_3$)$_2$CHCO | [D-Tyr$^1$, D-Ala$^2$, D-Asp$^3$]-hp |
| [CH$_3$(CH$_2$)$_3$CO]$_2$O | CH$_3$(CH$_2$)$_3$CO | [D-Tyr$^1$, D-Ala$^2$, D-Asp$^3$]-hp |
| [(CH$_3$)$_3$CCO]$_2$O | (CH$_3$)$_3$CCO | [D-Tyr$^1$, D-Ala$^2$, D-Asp$^3$]-hp |

The superscripts used in this Example, which are assigned to given amino acid residues, indicate the locations of said residues in the amino acid sequence of the synthesized growth hormone-releasing peptides.

EXAMPLE 17

Protected D-tyrosine-10, Human Pancreatic Growth Hormone-Releasing factor(9–29)-benzhydrylamine resin Benzhydrylamine polystyrene resin (commercially available from Bachem, Inc., Torrance, Calif.) (6.0 g, 3.00 mmol) in the chloride ion form is placed in the reaction vessel of a Beckman 990 automatic peptide synthesizer programmed to carry out the following work-wash cycle: (a) $CH_2Cl_2$; (b) 33% trifluoroacetic acid in $CH_2Cl_2$ (two times for one and 25 minutes each); (c) $CH_2Cl_2$; (d) $C_2H_5OH$; (e) $CH_2Cl_2$; (f) 10% $(C_2H_5)_3N$ in $CHCl_3$ (two times for two minutes each); and (g) $CH_2Cl_2$.

The neutralized resin is stirred with t-butyl-oxycarbonyl(Boc)-N-tosyl-1-arginine [Boc-Arg(Tos)] and diisopropylcarbodiimide (6 mmol) in $CH_2Cl_2$ for one hour, and the resulting amino acid resin is then cycled through the steps (a) through (g) in the above wash program. The following D-amino acids (3 mmol) are then coupled successively by the same reaction cycle: Boc-Ser(benzyl), Boc-Met, Boc-Ile, Boc-Asp(benzyl), Boc-Gln, Boc-Leu, Boc-Leu, Boc-Lys(4-chlorocarbenzoxy), Boc-Arg(Tos), Boc-Ala, Boc-Ser(benzyl), Boc-Leu, Boc-Gln, Boc-Gly, Boc-Leu, Boc-Val, Boc-Lys(4-chlorocarbenzoxy), Boc-Arg(tosyl), Boc-D-Tyr(4-bromocarbenzoxy) and Boc-Ser(benzyl), except that Boc-Gln is coupled in the presence of 1-hydroxybenzotriazole (6mmol) in dimethylformamide solution.

The completed peptide-benzhydrylamine resin, with the N-terminal Boc group removed, is then washed with $CH_3OH$ and air dried to give 11.79 g of material.

EXAMPLE 18

Preparation of Protected D-tyrosine-10-human Pancreatic-Growth Hormone-Releasing Factor (1–29)-benzhydrylamine resin Peptide benzhydrylamine resin (0.98 g, 0.25 mmol) containing the 9–29 residues of the peptide as described in Example 17 is subjected to the work-wash cycle also described in Example 17. The neutralized resin is stirred with Boc-L-asparagine (0.75 mmol), diisopropylcarbodiimide (0.75 mmol), and 1-hydroxybenzotriazole (0.75 mmol) in dimethylformamide.

The following amino acid derivatives (0.75 mmol) are then coupled successively by the same treatment cycle described in Example 17: Boc-Thr (benzyl), Boc-Phe, Boc-Ile, Boc-Ala, Boc-Asp(benzyl), Boc-Ala, and Boc-Tyr. The completed 1–29 peptide resin is then cycled through the standard work-wash program described in Example 17 in order to remove the N-terminal Boc group.

EXAMPLE 19

Preparation of D-tyrosine-10-human Pancreatic Growth Hormone-Releasing(1–29)-amine [(D-Tyr$^{10}$)-hpGRF(1–29)-NH$_2$]

A mixture of the 1–29 peptide resin described in Example 18 (0.25 mmol) and a solution of hydrogen fluoride (10 mL), dimethylsulfide (26 mL), and p-cresol (4 mL) are stirred at 0° C. for 75 minutes. Excess reagents are then rapidly evaporated under a stream of dry nitrogen and hydrogen fluoride (35 mL) is added, and the mixture stirred for a further 45 minutes at 0° C. Excess hydrogen fluoride is evaporated under nitrogen, and the resin plus free peptide are washed free of p-cresol with a large volume of diethyl ether.

The peptide is extracted into 50% acetic acid solution and applied to a column (2.5×95 cm) of Sephadex G-50 which is eluted with 2M acetic acid. Eluant is monitored at 280 nM and fractions containing a major uv-absorbing peak are pooled and lyophilized. A solution of the lyophilized powder is eluted on a column (1.5×45 cm) of octadecylsilane silica having a mesh size of 15-20M and pore size of 300 A° (purchased from Vydac, Hesperia, Calif.). A linear elution gradient of 15-50% acetonitrile in 0.1% trifluoroacetic acid solution was employed at a pumping pressure of about 80 psi. Emerging fractions are monitored at 280 nm and are each examined by analytical hplc at a wave length of 215 nm in order to ensure maximum homogeneity of pooled fractions. Lyophilization of these gave the title peptide as a white powder (32 mg).

This material gives one peak emerging at 38 minutes using analytical hplc on a column (0.4×25 cm) of Vydac octadecylsilane silica (5M mesh size, 300 A°) which is pumped at 2 mL/min with a linear gradient of 20 to 40% acetonitrile in 0.1% trifluoracetic acid. Product yield is 75 mg from 0.25 mmole of starting material.

Hplc elution time=27.9 minutes

Amino acid analysis gives: Asp, 31.0; Thr, 0.97; Ser, 2.81; Glu, 2.21; Gly, 105; Ala, 3.11; Val, 0.78; Met, 0.94; Ile, 1.70; Tyr, 2.00; Phe, 0.95; Lys, 1.85; Arg, 2.90.

EXAMPLE 20

Preparation of Protected N-acetyl-tosyl-L-histidine-1,D-alanine-2,L-norleucine-27-human Pancreatic Growth Hormone-Releasing factor (1–29)-benzhydrylamine resin Protected N-acetyl-tosyl-D-histidine-1,D-alanine-2,L-norleucine-27-human pancreatic growth hormone-releasing factor (1–29)-benzhydrylamine resin prepared as described in Example 14, except that in addition to placing L-tosyl-histidine in position 1 and D-alanine in position 2, L-norleucine is substituted for methionine in position 27, to yield the above-said benzhydrylamine resin.

EXAMPLE 21

Preparation of N-acetyl-L-histidine-1,D-alamine-2,L-norleucine-27-human Pancreatic Growth Hormone-Releasing (1–29)-amine The N-acetyl-tosyl-D-histidine-1,D-alanine-2,L-norleucine-27-human pancreatic growth hormone-releasing factor(1–29)-benzhydrylamine resin, from Example 14, is treated with hydrogen fluoride, dimethyl sulfide and p-creasol, as described in Example 3. Excess reagents are removed from the mixture by evaporation under a stream of dry nitrogen. The mixture is treated with hydrogen fluoride and excess hydrogen fluoride is again removed by evaporation under nitrogen. Diethyl ether is used to wash any free p-cresol from the resin and free peptide. Purification by the procedure of Example 3 yields: [(N-acetyl-His$^1$,D-Ala$^2$, Nle$^{27}$)-hpGRF-(1–29)NH$_2$]. Product yield is 124 mg from 0.25 mmole of starting material. Hplc elution time (flow rate 1.5 mL minutes) is 31.2 minutes. Amino acid analysis gives: Asp, 3.24; Thr, 1.01; Ser, 2.97; Glu, 2.40; Gly, 1.11; Ala, 3.18; Val, 0.76; Ile, 1.63; Tyr, 1.03; Phe, 0.92; His, 1.08; Lys, 1.78; Arg, 2.99, Nle, 0.85.

EXAMPLE 22

Preparation of D-alanine-2,D-tyrosine-10-human Pancreatic Growth-Releasing Factor(1–29)-benzhydrylamine Resin Peptide-benzhydrylamine resin (0.25 mmol) prepared in Example 17 is subjected to the coupling cycles described in Example 18, except that D-alanine is used in place of L-alanine in position 2.

EXAMPLE 23

Preparation of D-alanine-2,D-tyrosine-10-human Pancreatic Growth Hormone-Releasing(1–29)-amine[(D-Ala$^2$,D-Tyr$^{10}$)-hpGRF(1–29)-NH$_2$]

The peptide resin (0.25 mmol) described in Example 22 is treated with hydrogen fluoride mixtures and purified as described in Example 19. The purified, lyophilized peptide weighs 130 mg. Hplc elution time is 28.3 minutes using the analytical Hplc conditions as described in Example 19. Amino acid analysis of a 6M HCl hydrolysate gives the following amino acid ratios: Asp, 2.91; Thr, 0.97; Ser, 2.84; Glu, 2.20; Gly, 1.07; Ala, 3.00; Val, 0.96; Met, 0.59; Ile, 1.86; Leu, 4.08; Tyr, 1.86; Phe, 0.93; Lys, 1.99; Arg, 3.07.

EXAMPLE 24

Preparation of D-serine-9-human Pancreatic Growth Hormone-Releasing Factor(1–29)-benzhydrylamine Resin Peptide-benzhydrylamine resin (0.25 mmole) prepared in Example 17, except that D-serine is used in place of L-serine in position. 9, is subjected to the coupling cycles described in Example 18.

EXAMPLE 25

Preparation of D-serine-9-human Pancreatic Growth Hormone-Releasing(1–29)-amine[(D-Ser$^9$)-hpGRF(1–29)-NH$_2$]

The peptide resin (0.25 mmol) described in Example 24 is treated with hydrogen fluoride mixtures and purified as described in Example 19. The purified, lyophilized peptide weighs 108 mg. This material gives one peak emerging at 28.5 minutes using the analytical Hplc conditions as described in Example 19. Amino acid analysis of a 6M HCl hydrolysate gives the following amino acid ratios: Thr, 0.95; Ser, 2.80; Glu, 2.16; Gly, 1.02; Ala, 3.04; Val, 0.90; Ile, 1.75; Leu, 4.00; Tyr, 1.91; Phe, 0.92; Lys, 2.06; Arg, 3.85; Met, 0.90.

EXAMPLE 26

Evaluation of Peptide Effects on Growth Hormone Release in Mammals Using the Rat as the Test Species In this evaluation, the procedures described by W. A. Murphy et al., Endocrinology 109:491–495 (1980), were employed.

In growth hormone (GH) experiments, male rats (Charles Rivers) were anesthetized with NEMBUTAL ® (6 mg per 100 g body weight) which also served to maintain stimulated plasma GH levels. Exactly 30 minutes after the rats were anesthetized, 0.5 mL of saline or the test peptide in saline was administered as a SC bolus. A 1 mL blood sample was drawn from the jugular vein 15 minutes after the injection of the peptide in saline. GH levels were determined using NIADDKD rat GH RIA components.

| hpGRF(1-29)-NH₂ Structure-Activity Studies | | |
|---|---|---|
| Analog | Dose (μ/100 g BW) | Plasma GH (Ng/mL) |
| Saline | — | 333 ± 50 (5)* |
| [N-Ac-D-Tyr¹, D-Ala²]-hpGRF(1-29)-NH₂ | 0.5 | 499 ± 50 (5) |
| [N-AC-D-Tyr¹, D-Ala²]-hpGRF(1-29)-NH₂ | 0.2 | 680 ± 100 (7) |
| [N-Ac-D-Tyr¹, D-Ala²]-hpGRF(1-29)-NH₂ | 0.8 | 2063 ± 251 (6) |
| [N-Ac-D-Tyr¹, D-Ala²]-hpGRF(1-29)-NH₂ | 3.2 | 3818 ± 412 (6) |
| Saline | — | 27% ± 54 (11)* |
| [Arg¹², ²¹]-hpGRF(1-29)-NH₂ | 10 | 688 ± 84 (8) |
|  | 25 | 1613 ± 302 (8) |
| [N-Ac-Tyr, Arg¹², ²¹]-hpGRF(1-29)-NH₂ | 1 | 796 ± 88 (8) |
|  | 2.5 | 1649 ± 167 (8) |
| Saline | — | 309 ± 20 (6)* |
| [D-Ala², Arg¹², ²¹]-hpGRF(1-29)-NH₂ | 0.4 | 755 ± 131 (6) |
|  | 1.0 | 1752 ± 289 (6) |

| GRF(1-29)-NH₂ Analog | Dose (ug/100 g BW) | Plasma GH* (ng/ml) |
|---|---|---|
| Saline | — | 366 ± 81 (6) |
| (a) D-Asn⁸ | 4 | 1296 ± 118 (5) |
| " | 10 | 2397 ± 246 (6) |
| Saline | — | 278 ± 37 (6) |
| (b) D-Ala²-Nle²⁷ | 0.1 | 465 ± 75 (6) |
| " | 1.0 | 2287 ± 265 (6) |
| Saline | — | 214 ± 29 (6) |
| (c) His¹-D-Ala²-Nle²⁷ | 0.1 | 904 ± 111 (6) |
| " | 1.0 | 3379 ± 389 (6) |
| Saline | — | 203 ± 39 (8) |
| (d) D-Ala²-D-Asn⁸-Nle²⁷ | 0.05 | 407 ± 53 (6) |
| " | 0.5 | 1613 ± 138 (6) |
| Saline | — | 383 ± 79 (6) |
| (e) D-Asp³-D-Asn⁸-Nle²⁷ | 0.1 | 810 ± 86 (6) |
| " | 1.0 | 3213 ± 590 (6) |
| (f) D-Ala²-D-Asp³-D-Asn⁸-Nle²⁷ | 0.1 | 767 ± 146 (6) |
| " | 1.0 | 2419 ± 252 (6) |
| Potencies were determined by comparison to pooled standards: | | |
| GRF(1-29)-NH₂ | 10 | 1185 ± 74 (78) |
| " | 25 | 2570 ± 121 (70) |

| Analog | Dose (μg/100 g BW) | Plasma GH (ng/mL) |
|---|---|---|
| Saline | — | 454 ± 62 (6)* |
| hpGRF(1-29)-NH₂ | 10.0 | 2057 ± 187 (5) |
| hpGRF(1-29)-NH₂ | 25.0 | 4033 ± 284 (6) |
| [D-Ala²]-hpGRF(1-29)-NH₂ | 0.08 | 1118 ± 158 (6) |
| [D-Ala²]-hpGRF(1-29)-NH₂ | 0.20 | 2122 ± 350 (5) |
| [D-Ala²]-hpGRF(1-29)-NH₂ | 0.50 | 3539 ± 109 (5) |
| Saline | — | 541 ± 64 (13) |
| hpGRF(1-29)-NH₂ | 10.0 | 1627 ± 380 (6) |
| hpGRF(1-29)-NH₂ | 25.0 | 2520 ± 420 (5) |
| [D-Tyr¹]-hpGRF(1-29)-NH₂ | 1.2 | 1463 ± 263 (6) |
| [D-Tyr¹]-hpGRF(1-29)-NH₂ | 3.0 | 3247 ± 622 (6) |
| Saline | — | 342 ± 53 (9) |
| hpGRF(1-29)-NH₂ | 7.2 | 1686 ± 255 (6) |
| hpGRF(1-29)-NH₂ | 18.0 | 2842 ± 295 (6) |
| N-Ac-hpGRF(1-29)-NH₂ | 1.20 | 2518 ± 598 (5) |
| N-Ac-hpGRF(1-29)-NH₂ | 3.0 | 4899 ± 557 (6) |
| Saline | — | 301 ± 53 (5) |
| [D-Asp³]-hpGRF(1-29)-NH₂ | 5.0 | 3749 ± 808 (5) |
| Saline | — | 541 ± 78 (5) |
| [N-Ac-His¹, D-Ala²]-hpGRF(1-29)-NH₂ | 1.0 | 1974 ± 274 (6) |
| [N-Ac-His¹, D-Ala²]-hpGRF(1-29)-NH₂ | 5.0 | 4989 ± 638 (6) |
| [N-Ac-D-Tyr¹, D-Ala², D-Asp³]-hpGRF(1-29)-NH₂ | 1.0 | 1181 ± 164 (5) |
| [N-Ac-D-Tyr¹, D-Ala², D-Asp³]-hpGRF(1-29)-NH₂ | 5.0 | 3594 ± 754 (4) |

| Analog | Dose | Plasma GH | % Potency |
|---|---|---|---|
| D-Ser⁹ | 16 | 1804 ± 312 (6) | 108 (77-151) |
| D-Ser⁹ | 40 | 3652 ± 370 (6) |  |
| D-Tyr¹⁰ | 8 | 1674 ± 586 (5) | 228 (257-331) |
| D-Tyr | 20 | 3975 ± 635 (5) |  |
| N-AcHis¹, D-Ala², Nle²⁷ | 0.5 | 1146 ± 143 (6) | 1574 (1112-2226) |
| N-AcHis¹, D-Ala², Nle²⁷ | 1.25 | 1907 ± 603 (6) |  |

*Number of rats in parenthesis.

EXAMPLE 27

Preparation of D-asparagine⁸-human Pancreatic Growth Hormone-Releasing(1-29)-amide [(D-Asn⁸)-hpGRF(1-29)-NH₂]

The peptide-benzhydrylamine resin (0.25 mmole of resin) prepared in Example 1 was subjected to the coupling cycles described in Example 2, except that D-asparagine was used in place of L-asparagine in position 8. The yield was 38 mg, and the peptide had HPLC elution time of 28 minutes at a flow rate of 1.5 mL/minutes. The amino acid analysis gave: Asp, 3.05; Thr, 0.95; Ser, 2.96; Glu, 2.21; Gly, 1.04; Ala, 3.02; Val, 0.95; Ile, 1.85; Leu, 2.00; Nle 0.97; Tyr, 2.10; Phe, 0.96; Lys, 1.97; Arg, 3.20.

EXAMPLE 28

Preparation of D-alanine², Norleucine²⁷-human Pancreatic Growth Hormone-Releasing(1-29)-amide [(D-Ala², Nle²⁷)-hpGRF(1-29)-NH₂]

The peptide-benzhydrylamine resin was prepared as in Example 1 with L-norleucine replacing L-methionine in position 27 of the coupling cycle. A Boc protecting group on L-norleucine was used. This material was then coupled in the manner described in Example 2 with D-alanine relacing L-alanine in position 2. The yield was 71 mg from 0.25 mmole of resin used, and the HPLC elution time was 28.5 minutes with a flow rate of 1.5 mL/minutes. The amino acid analysis gave: Asp, 3.06; Thr, 1.00; Ser, 2.96; Glu, 2.20; Gly, 1.06; Ala, 3.10; Val, 0.90; Ile, 1.78; Leu, 4.08; Nle, 1.00; Tyr, 1.96; Phe, 0.88; Lys, 2.00; Arg, 3.14.

EXAMPLE 29

Preparation of Histidine¹, D-alanine², Norleucine²⁷-human Pancreatic Growth Hormone-Releasing(1-29)-amide [(His¹,D-Ala², Nle²⁷)-hpGRF(1-29)-NH₂]

The peptide-benhydrylamine resin was prepared as in Example 1 with L-norleucine replacing L-methionine in position 27 of the coupling cycle. This material was then coupled in the manner described in Example 2 with L-histidine replacing L-tyrosine in position 1 and D-alanine replacing L-alanine in position 2. The yield was 23 mg from 0.25 mmole of resin used, and the HPLC elution time was 27.5 minutes at a flow rate of 1.5 mL/minutes. The amino acid analysis gave: Asp, 3.13; Thr, 1.00; Ser, 2.98; Glu, 2.27; Gly, 1.10; Ala, 3.15; Val, 0.99; Ile, 1.88; Leu, 4.20; Nle, 1.05; Tyr, 0.98; Phe, 0.91; His, 1.17; Lys, 2.01; Arg, 3.11.

EXAMPLE 30

Preparation of D-alanine$^2$, D-asparagine$^8$, Norleucine$^{27}$-human Pancreatic Growth Hormone-Releasing(1–29)-amide [(D-Ala$^2$, D-Asn$^8$, Nle$^{27}$)-hpGRF(1–29)-NH$_2$]

The peptide-benzhydryl resin was prepared as in Example 1 with L-norleucine replacing L-methionine in position 27 of the coupling cycle. This material was then coupled in the manner described in Example 2 with D-alanine replacing L-alanine in position 2 and D-asparagine replacing L-asparagine in position 8. The yield was 41 mg from 0.25 mmole of resin used, and the HPLC elution time was 28.5 minutes at a flow rate of 1.5 mL/minutes. The amino acid analysis gave: Asp, 2.99; Thr, 1.00; Ser, 2.87; Glu, 2.14; Gly, 1.06; Ala, 3.04; Val, 0.93; Ile, 1.80; Leu; 4.02; Nle, 0.98; Tyr, 1.99; Phe, 0.90; Lys, 2.01; Arg, 3.08.

EXAMPLE 31

Preparation of D-aspartic acid$^3$, D-asparagine$^8$, Norleucine$^{27}$-human Pancreatic Growth Hormone-Releasing(1–29)-amide [(D-Asp$^3$, D-Asn$^8$, Nle$^{27}$)-hpGRF(1–29)-NH$_2$]

The peptide-benzhydryl resin was prepared as in Example 1 with L-norleucine replacing L-methionine in position 27 of the coupling cycle. This material was then coupled in the manner described in Example 2 with D-aspartic acid replacing L-aspartic acid in position 3 and D-asparagine replacing L-asparagine in position 8. The yield was 114 mg starting with 0.25 mmole of resin, and the HPLC elution time was 29.1 minutes at a flow rate of 1.5 mL/minutes. The amino acid analysis gave: Asp, 2.99; Thr, 1.00; Ser, 2.85; Glu, 2.16; Gly, 1.03; Ala, 3.03; Val, 0.94; Ile, 1.82; Leu, 4.03; Nle, 0.99; Tyr, 1.97; Phe, 0.92; Lys, 2.06; Arg, 3.05.

EXAMPLE 32

Preparation of D-alanine$^2$, D-aspartic acid$^3$, D-asparagine$^8$, Norleucine27-human Pancreatic Growth Hormone-Releasing(1–29)-amide [(D-Ala$^2$, D-Asp$^3$, D-Asn$^8$, Nle$^{27}$)-hpGRF(1–29)-NH$_2$]

The peptide-benzhydryl resin was prepared as in Example 1 with L-norleucine replacing L-methionine in position 27 of the coupling cycle. This material was then coupled in the manner described in Example 2 with D-alanine replacing L-alanine in position 2, D-aspartic acid replacing L-aspartic acid in position 3 and D-asparagine replacing L-asparagine in position 8. The yield was 67 mg starting with 0.25 mmole of resin, and the HPLC elution time was 28 minutes at a flow rate of 1.5 mL/minutes. The amino acid analysis gave: Asp, 3.01; Thr, 1.00; Ser, 2.90; Glu, 2.20; Gly, 1.05; Ala, 3.08; Val, 0.95; Ile, 1.86; Leu, 4.01; Nle, 0.96; Tyr, 1.95; Phe, 0.93; Lys, 2.05; Arg, 3.11.

EXAMPLE 33

Preparation of Arginine$^{12,21}$-human Pancreatic Growth Hormone-Releasing (1–29)-amide[Arg$^{12,21}$-hpGRF(1–29)-NH$_2$ The peptide resin is prepared as in Example 1 with L-arginine replacing D-lysine in positions 12 and 21 in the coupling cycle. This material is then coupled in the manner described in Example 2. The title product is then isolated by the usual manner.

EXAMPLE 34

Preparation of Protected N-acetyl Arginine$^{12,21}$-human Pancreatic Growth Hormone-Releasing Factor (1–29)-amide [N-AcTyr,Arg$^{12,21}$-hpGRF(1–29)-NH$_2$ The title compound is prepared by the method described in Example 4 and purified by standard techniques.

EXAMPLE 35

Preparation of D-alanine$^2$, Arginine$^{12,21}$-human Growth Hormone-Releasing (1–29)-amide[(D-Ala$^2$,Arg$^{12,21}$)-hpGRF (1–29)-NH$_2$ The peptide-benzhydryl resin is prepared as in Example 1 with L-arginine replacing L-lysine in positions 12 and 21 of the coupling cycle. This material is coupled in the manner described in Example 2 with D-alanine replacing L-alanine in position 2. The title peptide is isolated and purified in the usual manner.

EXAMPLE 36

Preparation of D-alanine-2-human Pancreatic Growth Hormone-Releasing (1–29)-Carboxylic Acid (D-Ala$^2$)-hpGRF (1–29)-OH.

Boc-Arg (Tos)(3 mM) is coupled to the Merrifield hydroxymethyl resin by stirring 1,1'-carbonyldiimidazole (3 mM) in a mixture of DMF and CH$_2$Cl$_2$ (10 ml) with the blocked Arg at −5° C. for 0.5 hr and then adding 1.5 mmol of the resin. The mixture is stirred for 20 hr. at room temperature and the resin is collected by filtration, washed with CH$_2$Cl$_2$, DMF, CH$_2$Cl$_2$, ETOH and CH$_2$Cl$_2$, and dried. The coupled resin mixture is further acetylated with a mixture of pyridine and Ac$_2$O [20 ml, 1:1(v/v)] for 0.5 hr. to esterify any free hydroxymethyl resin and washed as before. The Boc-Arg(Tos)-resin is then coupled to the remaining requisite amino acids as described in Example 1 and Example 2 and further treated with HF and purified in the manner described in Example 3 to afford the title compound.

EXAMPLE 37

Preparation of D-alanine$^2$, Arginine$^{12,21}$-human Growth Hormone-Releasing (1–29)-Carboxylic Acid (D-Ala$^2$,Arg$^{12,21}$)-hpGRF(1–29)-OH In the manner described in Example 36, the title compound is prepared with L-arginine replacing L-lysine in positions 12 and 21 in the coupling cycle. The peptide is then purified in the usual manner.

EXAMPLE 38

Effect of D-Ala$^2$-GRF(1–29)NH$_2$ on Milk Production in Dairy Cows (Treatments Administered Subcutaneously)

In this test, treatments are administered using a Latin Square design using four cows. Each treatment period is 10 days, and the interval between treatments is 4 days.

There is a pre-treatment period of one week, at the end of which each cow receives an indwelling jugular catheter. Catheters are flushed daily with heparinized (500–1000 IU/ml) sterile saline to help maintain potency and are replaced as needed.

The drugs are solubilized in sterile saline and injected subcutaneously each day with the dosage based on the cow's weight. Dosages range from 0.06 mg/kg animal/- day to 60 mg/kg animal/day, preferably 0.10 mg/kg animal/day to 50 mg/kg/day.

On the first and last treatment days of each period, blood is collected at 15 minute intervals for 1 hour prior to and 1½ hours after treatment; sampling continues at 30 minutes intervals for an additional 3½ hours.

Milk samples are obtained on the evening proceeding each bleeding day, the morning of each bleeding day and combined (50% each).

Feed intake, refusals and milk production is monitored for all animals.

Results obtained are reported as mean milk production in kg/day for each treatment and compared against a saline control.

|  | D-Ala²-GRF(1–29)NH₂ 0.4 mg/kg/day | D-Ala²-GRF(1–29)NH₂ 0.8 mg/kg/day | Saline Control |
|---|---|---|---|
| Milk Production kg/day | 23.9 | 23.8 | 22.2 |
| % increase over control | +7.6% | +7.2% | — |

These results indicate that the growth hormone-releasing peptides of the present invention not only elevate growth hormone release but that the biological activity of increasing milk production in the subject animals is observed. This, of course, indicates that other biological responses, such as increased meat production, increasing growth rate, increasing wool production, etc. result by the administration of the present peptides to animals.

What is claimed is:

1. A peptide having a formula:

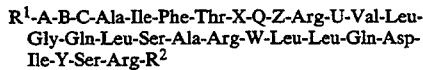

or

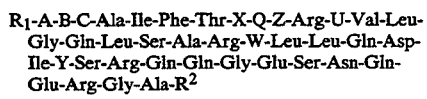

or

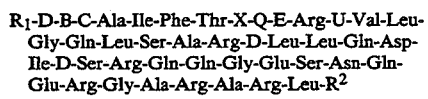

wherein $R^1$ is hydrogen or $C_1$–$C_6$ straight- or branched-chain alkanoyl; $R^2$ is $NR^3R^4$ or $OR^3$; $R^3$ and $R^4$ are selected from the group consisting of hydrogen and a straight-or branched-chain alkyl group containing one to six carbon atoms; A is tyrosyl, D-tyrosyl, histidyl, D-histidyl; B is D-alanyl or N-methyl-D-alanyl; C is aspartyl, D-aspartyl, glutamyl or D-glutamyl; Q is seryl or D-seryl; U is lysyl or arginyl; W is lysyl or arginyl; X is asparaginyl or D- asparaginyl; Y is norleucyl or methionyl, and Z is tyrosyl or D-tyrosyl; with the provisos that when U is arginyl, W is arginyl; and when B is N-methyl-D-alanyl, U and W are both arginyl; and the pharmaceutically acceptable salts thereof.

2. A peptide according to claim 1, wherein $R^1$ is selected from hydrogen or $C_1$–$C_3$ alkanoyl; $R^2$ is $NR^3R^4$; $R^3$ and $R^4$ are each selected from hydrogen and $C_1$–$C_3$ alkyl; A is tyrosyl, D-tyrosyl, histidyl; B is D-alanyl; C is aspartyl or D-aspartyl; Q is seryl or D-seryl; U is lysyl or arginyl; W is lysyl or arginyl; X is asparaginyl or D-asparaginyl; Y is norleucyl or methionyl, and Z is tyrosyl or D-tyrosyl; with the abovementioned provisos; and the pharmaceutically acceptable salts thereof.

3. A peptide according to claim 1, having the formula (I) structure wherein $R^1$ is selected from hydrogen or acetyl; $R^2$ is $NH_2$; A is tyrosyl, D-tyrosyl, or histidyl; B is D-alanyl; C is aspartyl or D-aspartyl; Q is seryl or D-seryl; U and W are each lysyl or each arginyl; X is asparaginyl or D- asparaginyl; Y is norleucyl or methionyl, and Z is tyrosyl or D-tyrosyl; with the above-mentioned provisos; and the pharmaceutically acceptable salts thereof.

4. The peptide according to claim 1 of the formula:
Tyr-D-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-NH₂ and its pharmaceutically acceptable salts.

5. The peptide according to claim 1 of the formula:
Ac-His-D-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-NH₂ and its pharmaceutically acceptable salts.

6. The peptide according to claim 1 of the formula:
Ac-D-Tyr-D-Ala-D-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-NH₂ and its pharmaceutically acceptable salts.

7. The peptide according, to claim 1 of the formula:
Ac-D-Tyr-D-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-NH₂ and its pharmaceutically acceptable salts.

8. The peptide according to claim 1 of the formula:
Tyr-D-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Nle-Ser-Arg-NH₂ and its pharmaceutically acceptable salts.

9. The peptide according to claim 1 of the formula:
His-D-Ala-Asp-Ala-Ile-Phe-Thr-D-Asn-Ser-Tyr-Arg-Lys-Val-Leu-Gly-Gln-Leu-Ser-Ala-Arg-Lys-Leu-Leu-Gln-Asp-Ile-Nle-Ser-Arg-NH₂ and its pharmaceutically acceptable salts.

10. The peptide according to claim 1 of the formula:
Tyr-D-Ala-Asp-Ala-Ile-Phe-Thr-D-Asn-Ser-Tyr-Arg-Lys-Val-Leu-Gly-Gln-Leu-Ser-Ala-Arg-Lys-Leu-Leu-Gln-Asp-Ile-Nle-Ser-Arg-NH₂ and its pharmaceutically acceptable salts.

11. The peptide according to claim 1 of the formula:
Tyr-D-Ala-D-Asp-Ala-Ile-Phe-Thr-D-Asn-Ser-Tyr-Arg-Lys-Val-Leu-Gly-Gln-Leu-Ser-Ala-Arg-Lys-Leu-Leu-Gln-Asp-Ile-Nle-Ser-Arg-NH₂ and its pharmaceutically acceptable salts.

12. The peptide according to claim 1 of the formula:
Ac-Tyr-D-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-NH₂ and its pharmaceutically acceptable salts.

13. The peptide according to claim 1 of the formula:
Ac-His-D-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gly-Asp-Ile-Nle-Ser-Arg-NH₂.

14. The peptide according to claim 1 of the formula:
Tyr-D-Ala-Asp-Ala-Ile-Phe-Thr-Asn-Ser-D-Tyr-Arg-Lys-Val-Leu-Gly-Gln-Leu-Ser-Ala-Arg-Lys-Leu-Leu-Gln-Asp-Ile-Met-Ser-Arg-NH₂.

15. The peptide according to claim 1 of the formula:
Tyr-D-Ala-Asp-Ala-Ile-Phe-Thr-Asn-Ser-Tyr-Arg-Arg-Val-Leu-Gly-Gln-Leu-Ser-Ala-Arg-Arg-Leu-Leu-Gln-Asp-Ile-Met-Ser-Arg-NH₂ and its pharmaceutically acceptable salts.

16. The peptide according to claim 1 of the formula:
Ac-D-Tyr-D-Ala-Asp-Ala-Ile-Phe-Thr-Asn-Ser-Tyr-Arg-Arg-Val-Leu-Gly-Gln-Leu-Ser-Ala-Arg-Arg-Leu-Leu-Gln-D-Asp-Ile-Met-Ser-Arg-NH₂ and its pharmaceutically acceptable salts.

17. The peptide according to claim 1 of the formula:
Tyr-D-Ala-Asp-Ala-Ile-Phe-Thr-Asn-Ser-Tyr-Arg-Arg-Val-Leu-Gly-Gln-Leu-Ser-Ala-Arg-Arg-Leu-Leu-Gln-Asp-Ile-Met-Ser-Arg-OH and its pharmaceutically acceptable salts.

18. The peptide according to claim 1 of the formula:
Tyr-D-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-OH and its pharmaceutically acceptable salts.

19. A method for increasing the release of growth hormone in a mammal, said method comprising: administering to said mammal an effective amount from 0.000001 to 0.1 mg/kg of mammalian body weight/day of a peptide having the formula,

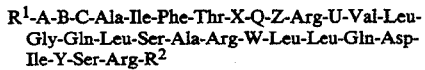

(I)

or

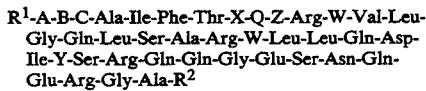

(II)

or

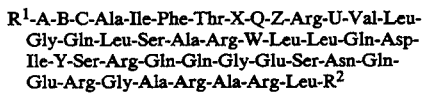

(III)

wherein R¹ is hydrogen or C₁–C₆ straight- or branched-chain alkanoyl; is R² is NR³R⁴ or OR³; R³ and R⁴ are selected from the group consisting of hydrogen and a straight- or branched-chain alkyl group containing one to six carbon atoms; A is tyrosyl, D-tyrosyl, histidyl, D-histidyl; B is D-alanyl or N-methyl-D-alanyl; C is aspartyl, D-aspartyl, glutamyl or D-glutamyl; Q is seryl or D-seryl; U is lysyl or arginyl; W is lysyl or arginyl; X is asparaginyl or D-asparaginyl; Y is norleucyl or methionyl, and Z is tyrosyl or D-tyrosyl; and the pharmaceutically acceptable salts thereof.

20. A method according to claim 19 wherein R¹ is selected from hydrogen or C₁–C₃ alkanoyl; R₂ is NR³R⁴; R³ and R⁴ are each selected from hydrogen and C₁–C₃ alkyl; A is tyrosyl, D-tyrosyl, or histidyl; B is D-alanyl; C is aspartyl or D-aspartyl; Q is seryl or D-seryl; U is lysyl or arginyl; W is lysyl or arginyl; X is asparaginyl or D-asparaginyl; Y is norleucyl or methionyl, and Z is tyrosyl or D-tyrosyl; and the pharmaceutically acceptable salts thereof.

21. A method according to claim 19, wherein the peptide is of the formula (I); R¹ is hydrogen or acetyl; R² is NH₂; A is tyrosyl, D-tyrosyl, or histidyl; B is D-alanyl; C is aspartyl or D-aspartyl; Q is seryl or D-seryl; U and W are each lysyl or each arginyl; X is asparaginyl or D-asparaginyl; Y is norleucyl or methionyl, and Z is tyrosyl or D-tyrosyl; and the pharmaceutically acceptable salts thereof.

22. A method according to claim 19, wherein the peptide is [D-Ala²]-hpGRF(1-29)-NH₂.

23. The method according to claim 19, wherein the peptide is Tyr-D-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Nle-Ser-Arg-NH₂ and its pharmaceutically acceptable salts.

24. The method according to claim 19, wherein the peptide is His-D-Ala-Asp-Ala-Ile-Phe-Thr-D-Asn-Ser-Tyr-Arg-Lys- Val-Leu-Gly-Gln-Leu-Ser-Ala-Arg-Lys-Leu-Leu-Gln-Asp-Ile-Nle-Ser-Arg-NH₂ and its pharmaceutically acceptable salts.

25. The method according to claim 19, wherein the peptide is Tyr-D-Ala-Asp-Ala-Ile-Phe-Thr-D-Asn-Ser-Tyr-Arg-Lys-Val-Leu-Gly-Gln-Leu-Ser-Ala-Arg-Lys-Leu-Leu-Gln-Asp-Ile-Nle-Ser-Arg-NH₂ and its pharmaceutically acceptable salts.

26. The method according to claim 19, wherein the peptide is Tyr-D-Ala-D-Asp-Ala-Ile-Phe-Thr-D-Asn-Ser-Tyr-Arg-Lys-Val-Leu-Gly-Gln-Leu-Ser-Ala-Arg-Lys-Leu-Leu-Gln-Asp-Ile-Nle-Ser-Arg-NH₂ and its pharmaceutically acceptable salts.

27. The method according to claim 19, wherein the peptide is Ac-Tyr-D-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-NH₂ and its pharmaceutically acceptable salts.

28. The method according to claim 19, wherein the peptide is Ac-His-D-Ala-Asp-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Nle-Ser-Arg-NH₂.

29. The method according to claim 1, wherein the peptide is Tyr-D-Ala-Asp-Ala-Ile-Phe-Thr-Asn-Ser-D-Tyr-Arg-Lys-Val-Leu-Gly-Gln-Leu-Ser-Ala-Arg-Lys-Leu-Leu-Gln-Asp-Ile-Met-Ser-Arg-NH₂.

30. A method according to claim 1, wherein the peptide is: Tyr-D-Ala-Asp-Ala-Ile-Phe-Thr-Asn-Ser-Tyr-Arg-Arg-Val-Leu-Gly-Gln-Leu-Ser-Ala-Arg-Arg-Leu-Leu-Gln-Asp-Ile-Met-Ser-Arg-NH₂ and its pharmaceutically acceptable salts.

31. A method according to claim 19, wherein the peptide is: Ac-D-Tyr-D-Ala-Asp-Ala-Ile-Phe-Thr-Asn-Ser-Tyr-Arg-Arg- Val-Leu-Gly-Gln-Leu-Ser-Ala-Arg-Arg-Leu-Leu-Gln-Asp-Ile-Met-Ser-Arg-NH₂ and its pharmaceutically acceptable salts.

32. A method according to claim 19, wherein the peptide is: Tyr-D-Ala-Asp-Ala-Ile-Phe-Thr-Asn-Ser-Tyr-Arg-Arg-Val-Leu-Gly-Gln-Leu-Ser-Ala-Arg-Agr-Leu-Leu-Gln-Asp-Ile-Met-Ser-Arg-OH and its pharmaceutically acceptable salts.

33. A method according to claim 19, wherein the peptide is: Tyr-D-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-OH and its pharmaceutically acceptable salts.

34. A method for increasing milk production in a dairy cow, said method comprising: administering to said cow a milk-production-increasing effective amount of a formula (I), (II) or (III) peptide, said peptide having a formula,

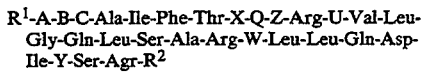    (I)

or

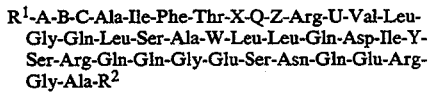    (II)

or

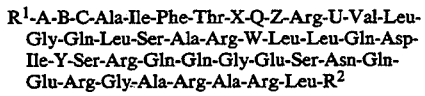    (III)

wherein R¹ is hydrogen or $C_1$–$C_6$ straight- or branched-chain alkanoyl; $R^2$ is $NR^3R^4$ or $OR^3$; $R^3$ and $R^4$ are selected from the group consisting of hydrogen and a straight- or branched-chain alkyl group containing one to six carbon atoms; A is tyrosyl, D-tyrosyl, histidyl, D-histidyl; B is D-alanyl or N-methyl-D-alanyl; C is aspartyl, D-aspartyl, glutamyl or D-glutamyl; Q is seryl or D-seryl; U is lysyl or arginyl; W is lysyl or arginyl; X is asparaginyl or D-asparaginyl; Y is norleucyl or methionyl, and Z is tyrosyl or D-tyrosyl; with the provisos that when H is lysyl, W is lysyl; and when U is arginyl, W is arginyl; and when B is N-methyl-D-alanyl, U and W are both arginyl; and the pharmaceutically acceptable salts thereof.

35. A method according to claim 34, wherein the peptide is [D-Ala²]-hp GRF(1–29)-NH₂.

36. A method for increasing the growth rate of an animal, said method comprising: administering to said animal a growth-promoting amount of a formula (I), (II) or (III) peptide having the formula,

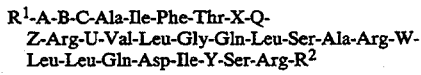    (I)

or

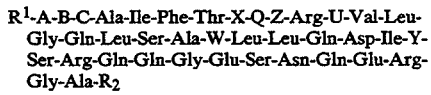    (II)

or

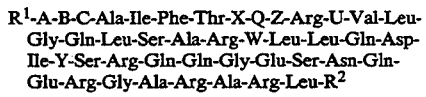    (III)

wherein R¹ is hydrogen or $C_1$–$C_6$ straight- or branched-chain alkanoyl; $R^2$ is $NR^3R^4$ or $OR^3$; $R^3$ and $R^4$ are selected from the group consisting of hydrogen and a straight- or branched-chain alkyl group containing one to six carbon atoms; A is tyrosyl, D-tyrosyl, histidyl, D-histidyl; B is D-alanyl or N-methyl-D-alanyl; C is aspartyl, D-aspartyl, glutamyl or D-glutamyl; Q is seryl or D-seryl; U is lysyl or arginyl; W is lysyl or arginyl; X is asparaginyl or D-asparaginyl; Y is norleucyl or methionyl, and Z is tyrosyl or D-tyrosyl; with the provisos that when H is lysyl, W is lysyl; and when U is arginyl, W is arginyl; and when B is N-methyl-D-alanyl, U and W are both arginyl; and the pharmaceutically acceptable salts thereof.

37. A process for the preparation of a peptide having the formula,

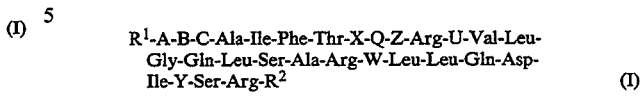    (I)

or

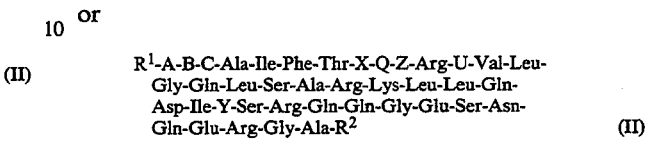    (II)

or

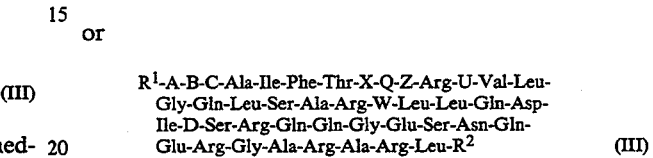    (III)

wherein R¹ is hydrogen or $C_1$–$C_8$ straight- or branched-chain alkanoyl; $R^2$ is $NR^3R^4$ or $OR^3$; $R^3$ and $R^4$ are selected from the group consisting of hydrogen and a straight- or branched-chain alkyl group containing one to six carbon atoms; A is tyrosyl, D-tyrosyl, histidyl or D-histidyl; B is D-alanyl or N-methyl-D-alanyl; C is aspartyl, D-aspartyl, glutamyl or D-glutamyl; Q is seryl or D-seryl; U is lysyl or arginyl; W is lysyl or arginyl; X is asparaginyl or D-asparaginyl; Y is norleucyl or methionyl, and Z is tyrosyl or D-tyrosyl; and the pharmaceutically acceptable salts thereof; said process comprising: attaching a C-terminal protected amino acid to a resin in the presence of a coupling agent; washing with an inert solvent; deprotecting in the presence of an acid; repeating this sequence with the subsequent protected amino acids as defined in formulas (I), (II) or (III), stepwise, from the C-terminus of the peptide; and finally detaching the peptide from the resin in the presence of an acid to afford the peptide of formulas (I), (II), or (III) wherein $R^2$ is NH₂, wherein said resin is BHA or p-ME-BHA; or detaching the peptide from the resin with ammonia, alkylamine or dialkylamine and deprotecting with an acid to afford the peptide of formulas (I), (II) or (III), wherein $R^2$ is $NR^3R^4$ wherein said resin is chloromethylated or hydroxymethylated resin; or detaching the peptide from the resin in the presence of an acid to afford the peptide of the formulas (I), (II) or (III) wherein $R^2$ is OH; wherein said resin is a chloromethylated or hydroxymethylated resin; or detaching the peptide from the resin in the presence of a base and an $R^3OH$ alcohol, followed by acid treatment to afford the peptide of the formulas (I), (II) or (III), wherein $R^2$ is $OR^3$, wherein $R^3$ is a straight- or branched-chain alkyl group containing one to six carbon atoms and said resin is a chloromethylated or hydroxymethylated resin.

38. A synthetic peptide, or a nontoxic salt thereof, having the formula: H-$R_1$-$R_2$-$R_3$-Ala-Ile-Phe-Thr-$R_8$-Ser-$R_{10}$-Arg-$R_{12}$-$R_{13}$-Leu-$R_{15}$-Gln-$R_{17}$-$R_{18}$-Ala-Arg-Lys-Leu-$R_{23}$-$R_{24}$-$R_{25}$-Ile-$R_{27}$-$R_{28}$-Arg-Gln-Gln-Gly-Glu-$R_{34}$-Asn-Gln-Glu-$R_{38}$-$R_{39}$-$R_{40}$-Arg-$R_{42}$-$R_{43}$-$R_{44}$-Y wherein $R_1$ is Tyr; $R_2$ is D-Ala; $R_3$ is Asp or D-Asp; $R_8$ is Asn; $R_{10}$ is Tyr; $R_{12}$ is Lys; $R_{13}$ is Val; $R_{15}$ is Gly; $R_{17}$ is Leu; $R_{18}$ is Ser; $R_{23}$ is Leu; $R_{24}$ is Gln; $R_{25}$ is Asp; $R_{27}$ is Met; $R_{28}$ is Ser; $R_{34}$ is Ser; $R_{38}$ is Arg; $R_{39}$ is Gly; $R_{40}$ is Ala; $R_{42}$ is Ala; $R_{43}$ is Arg; $R_{44}$ is Leu; and Y is the radical —COOR or —CON(R)(R') with R and R' being hydrogen; provided however, that any or all of the residues between $R_{29}$ and $R_{44}$, inclusive, may be deleted.

39. A pharmaceutical composition for stimulating the release of GH in an animal comprising an effective amount of the peptide of claim 38 or a nontoxic salt thereof, and a carrier thereof.

40. A method for the therapeutic treatment of a human which comprises administering an effective amount of a composition in accordance with claim 39.

41. A method of stimulating the release of growth hormone in an animal, which comprises administering to said animal an effective amount of a synthetic peptide having the sequence $R_1$-$R_2$-$R_3$-Ala-Ile-Phe-Thr-$R_8$-Ser-$R_{10}$-Arg-$R_{12}$-$R_{13}$-Leu-$R_{15}$-Gln-$R_{17}$-$R_{18}$-Ala-Arg-Lys-Leu-$R_{23}$-$R_{24}$-$R_{25}$-Ile-$R_{27}$-$R_{28}$-Arg-Gln-Gln-Gly-Glu-$R_{34}$-Asn-Gln-Glu-$R_{38}$-$R_{39}$-$R_{40}$-Arg-$R_{42}$-$R_{43}$-$R_{44}$ wherein $R_1$ is Tyr; $R_2$ is D-Ala; $R_3$ is Asp or D-Asp; $R_8$ is Asn; $R_{10}$ is Tyr; $R_{12}$ is Lys; $R_{13}$ is Val; $R_{15}$ is Gly; $R_{17}$ is Leu; $R_{18}$ is Ser; $R_{23}$ is Leu; $R_{24}$ is Gln; $R_{25}$ is Asp; $R_{27}$ is Met; $R_{28}$ is Ser; $R_{34}$ is Ser; $R_{38}$ is Arg; $R_{39}$ is Gly; $R_{40}$ is Ala; $R_{42}$ is Ala; $R_{43}$ is Arg; $R_{44}$ is Leu; provided however that any or all of the residues between $R_{29}$ and $R_{44}$, inclusive, may be deleted; or a nontoxic salt thereof.

42. A method for promotion of growth in a warm-blooded nonhuman animal in accordance with claim 41.

43. A method for growth promotion in aquiculture by administering to a fish an effective amount of a peptide accordance with claim 41.

44. A method of accelerating growth in a non-human animal, which method comprises administering to said animal an effective amount of a synthetic peptide having the sequence: $R_1$-$R_2$-$R_3$-Ala-Ile-Phe-Thr-$R_8$-Ser-$R_{10}$-Arg-$R_{12}$-$R_{13}$-Leu-$R_{15}$-Gln-$R_{17}$-$R_{18}$-Ala-Arg-Lys-Leu-$R_{23}$-$R_{24}$-$R_{25}$-Ile-$R_{27}$-$R_{28}$-$R_{29}$ wherein $R_1$ is Tyr; $R_2$ is D-Ala; $R_3$ is Asp or D-Asp; $R_8$ is Asn; $R_{10}$ is Tyr; $R_{12}$ is Lys; $R_{13}$ is Val; $R_{15}$ is Gly; $R_{17}$ is Leu; $R_{18}$ is Ser; $R_{23}$ is Leu; $R_{24}$ is Gln; $R_{25}$ is Asp; $R_{27}$ is Met; $R_{28}$ is Ser; and $R_{29}$ is Arg.

45. A synthetic peptide or a nontoxic salt thereof, having the sequence: $R_1$-$R_2$-$R_3$-Ala-Ile-Phe-Thr-$R_8$-Ser-$R_{10}$-Arg-$R_{12}$-$R_{13}$-$R_{14}$-$R_{15}$-Gln-$R_{17}$-$R_{18}$-Ala-Arg-Lys-Leu-$R_{23}$-$R_{24}$-$R_{25}$-Ile-$R_{27}$-$R_{28}$-$R_{29}$-Gln-Gln-Gly-Glu-$R_{34}$-Asn-Gln-Glu-$R_{38}$-$R_{39}$-$R_{40}$-Arg-$R_{42}$-$R_{43}$-$R_{44}$ wherein $R_1$ is Tyr; $R_2$ is D-Ala or D-NMA; $R_3$ is Asp or D-Asp; $R_8$ is Asn; $R_{10}$ is Tyr; $R_{12}$ is Lys; $R_{13}$ is Val; $R_{14}$ is Leu; $R_{15}$ is Gly; $R_{17}$ is Leu; $R_{18}$ is Ser; $R_{23}$ is Leu; $R_{24}$ is Gln; $R_{25}$ is Asp; $R_{27}$ is Met; $R_{28}$ is Ser; $R_{29}$ is Arg; $R_{34}$ is Ser; $R_{38}$ is Arg; $R_{39}$ is Gly; $R_{40}$ is Ala; $R_{42}$ is Ala; $R_{43}$ is Arg; $R_{44}$ is Leu; provided however that any or all of the residues between $R_{29}$ and $R_{44}$, inclusive, may be deleted.

46. The peptide of claim 45 wherein $R_2$ is D-NMA.

47. The peptide of claim 46 wherein $R_3$ is Asp, $R_8$ is Asn, $R_{10}$ is Tyr, $R_{12}$ is Lys, $R_{13}$ is Val, $R_{15}$ is Gly, $R_{18}$ is Ser, $R_{24}$ is Gln, $R_{28}$ is Ser, $R_{34}$ is Ser, $R_{38}$ is Arg, $R_{39}$ is Gly, $R_{40}$ is Ala, $R_{42}$ is Ala, $R_{43}$ is Arg and $R_{44}$ is Leu.

48. A pharmaceutical composition for stimulating the release of GH in an animal comprising an effective amount of the peptide of claim 45 or a nontoxic salt thereof, and a pharmaceutically or veterinarily acceptable liquid or solid carrier therefor.

49. A method for the therapeutic treatment of a human which comprises administering to said human an effective amount of a composition in accordance with claim 48.

50. A method of stimulating the release of growth hormone in an animal, which comprises administering to said animal an effective amount of a synthetic peptide, or a nontoxic salt thereof, having the sequence: $R_1$-$R_2$-$R_3$-Ala-Ile-Phe-Thr-$R_8$-Ser-$R_{10}$-Arg-$R_{12}$-$R_{13}$-$R_{14}$-$R_{15}$Gln-$R_{17}$$R_{18}$-Ala-Arg-Lys-Leu-$R_{23}$-$R_{24}$-$R_{25}$-Ile-$R_{27}$-$R_{28}$-$R_{29}$-Glu-$R_{38}$-$R_{39}$-$R_{40}$-Arg-$R_{42}$-$R_{43}$-$R_{44}$ wherein $R_1$ is Tyr; $R_2$ is D-Ala or D-NMA; $R_3$ is Asp or D-Asp; $R_8$ is Asn; $R_{10}$ is Tyr; $R_{12}$ is Lys; $R_{13}$ is Val; $R_{14}$ is Leu; $R_{15}$ is Gly; $R_{17}$ is Leu; $R_{18}$ is Ser; $R_{23}$ is Leu; $R_{24}$ is Gln; $R_{25}$ is Asp; $R_{27}$ is Met; $R_{28}$ is Ser; $R_{29}$ is Arg; $R_{34}$ is Ser; $R_{38}$ is Arg; $R_{39}$ is Gly; $R_{40}$ is Ala; $R_{42}$ is Ala; $R_{43}$ is Arg; $R_{44}$ is Leu; provided however that any or all of the residues between $R_{29}$ and $R_{44}$, inclusive, may be deleted.

51. A method for promotion of growth in a warm-blooded animal in accordance with claim 50.

52. A method for growth promotion in aquiculture by administering to a fish an effective amount of a peptide in accordance with claim 50.

53. A method of accelerating growth in a nonhuman animal, which method comprises administering to said animal an effective amount of a synthetic peptide having the sequence: $R_1$-$R_2$-$R_3$-Ala-Ile-Phe-Thr-$R_8$-Ser-$R_{10}$-Arg-$R_{12}$-$R_{13}$-$R_{14}$-$R_{15}$-Gln-$R_{17}$-$R_{18}$-Ala-Arg-Lys-Leu-$R_{23}$-$R_{24}$-$R_{25}$-Ile-$R_{27}$-$R_{28}$-$R_{29}$-$NH_2$ wherein $R_1$ is Tyr; $R_2$ is D-Ala or D-NMA; $R_3$ is Asp or D-Asp; $R_8$ is Asn; $R_{10}$ is Tyr; $R_{12}$ is Lys; $R_{13}$ is Val; $R_{14}$ is Leu; $R_{15}$ is Gly; $R_{17}$ is Leu; $R_{18}$ is Ser; $R_{23}$ is Leu; $R_{24}$ is Gln; $R_{25}$ is Asp; $R_{27}$ is Met; $R_{28}$ is Ser; $R_{29}$ is Arg; or a nontoxic salt thereof.

* * * * *